United States Patent

Johnson

[11] Patent Number: 5,966,477
[45] Date of Patent: Oct. 12, 1999

[54] FIBER OPTIC SENSOR ENCLOSURE SYSTEM

[76] Inventor: Douglas M. Johnson, 13247 Seventh Ave. NW., Seattle, Wash. 98177

[21] Appl. No.: 08/900,260

[22] Filed: Jul. 25, 1997

Related U.S. Application Data

[63] Continuation-in-part of application No. 08/687,754, Jul. 25, 1996, Pat. No. 5,712,934.

[51] Int. Cl.⁶ .................................................. G02B 6/00
[52] U.S. Cl. .............................. 385/12; 385/13; 385/123; 250/339.11; 356/133
[58] Field of Search .............................. 385/12, 123, 141, 385/13; 250/339.11, 341.2, 341.8; 356/133

[56] References Cited

U.S. PATENT DOCUMENTS

| | | |
|---|---|---|
| 3,120,125 | 2/1964 | Vasel . |
| 3,384,885 | 5/1968 | Forbush . |
| 3,535,933 | 10/1970 | Pliml, Jr. . |
| 3,548,657 | 12/1970 | Panerai et al. . |
| 3,553,666 | 1/1971 | Melone . |
| 3,683,196 | 8/1972 | Obenhaus . |
| 3,834,235 | 9/1974 | Bouton et al. . |
| 3,895,235 | 7/1975 | Melone . |
| 3,995,169 | 11/1976 | Oddon . |
| 4,009,382 | 2/1977 | Nath .......................................... 385/12 |
| 4,038,650 | 7/1977 | Evans et al. . |
| 4,082,959 | 4/1978 | Nakashima . |
| 4,156,149 | 5/1979 | Vaccari . |
| 4,187,025 | 2/1980 | Harmer . |
| 4,270,049 | 5/1981 | Tanaka et al. . |
| 4,274,705 | 6/1981 | Miller . |
| 4,287,427 | 9/1981 | Scifres . |
| 4,311,048 | 1/1982 | Merz . |
| 4,403,826 | 9/1983 | Presby . |
| 4,435,091 | 3/1984 | Nedreski . |
| 4,851,817 | 7/1989 | Brossia et al. . |
| 4,899,047 | 2/1990 | Cry et al. . |
| 4,906,845 | 3/1990 | Bellhouse et al. . |
| 5,005,005 | 4/1991 | Brossia et al. . |
| 5,291,032 | 3/1994 | Vali et al. . |
| 5,330,073 | 7/1994 | Collins et al. . |
| 5,362,971 | 11/1994 | McMahon et al. . |
| 5,422,495 | 6/1995 | Cohn . |
| 5,462,880 | 10/1995 | Kane et al. . |
| 5,585,634 | 12/1996 | Stevenson et al. . |
| 5,712,934 | 1/1998 | Johnson ..................................... 385/12 |

FOREIGN PATENT DOCUMENTS 34 25 715 A1   1/1986   Germany .

OTHER PUBLICATIONS

Carome, Edward F., et al., "Fiber–Optic Sensor System for Hydrocarbon Vapors," *Sensors and Actuators B* 13–14, 1993, pp. 305–308.

Cary, J.W., et al., "Using an Electro–Optical Switch to Measure Soil Water Suction," *Soil Science Society of America Journal,* vol. 55, No. 6, Nov.–Dec. 1991, pp. 1798–1800.

Fibertron®, Buena Park, CA, product catalog, vol. V, pp. 1, 4–8 through 4–15.

*Primary Examiner*—Phan T. H. Palmer
*Attorney, Agent, or Firm*—Christensen O'Connor Johnson & Kindness PLLC

[57] ABSTRACT

There is disclosed a sensor system comprising a sensor for detecting and signaling the presence of a fluid in an enclosure. The sensor system can be installed or incorporated within electronics and communications enclosures that house fluid-sensitive components and is useful in the early detection and warning of fluid leaks into such enclosures. In addition to the sensor, the system includes a means for conducting fluids entering the enclosure to the sensor and absorbent material to absorb any entering fluid.

35 Claims, 13 Drawing Sheets

FIBER OPTIC SENSOR ENCLOSURE SYSTEM

CROSS-REFERENCE TO RELATED APPLICATION

This application is a continuation-in-part of U.S. patent application Ser. No. 08/687,754, filed Jul. 25, 1996 now U.S. Pat. No. 5,712,934, priority of the filing date of which is hereby claimed under 35 U.S.C. § 120.

FIELD OF THE INVENTION

The present invention relates in general to a sensor system, and more particularly to a sensor system that includes a fiber optical sensor for detecting and signaling the presence of fluids.

BACKGROUND OF THE INVENTION

Briefly, fiber optic technology relates to the transmission of light through a light conducting material such as optical glass, fused silica, and certain plastics. The choice of a particular material depends on the intended use of the light transmission system, and takes into consideration the properties of the fiber including its refractive index, light transmittance, as well as thermal and chemical characteristics. The size (e.g., diameter and length) and configuration of the fiber optic device is also selected based on the intended use. Devices derived from light conducting materials having relatively large diameters are referred to as light pipes. In contrast, thin filaments having significantly smaller radii (e.g., from 100 to 3,000 micrometers, $\mu$m) are commonly referred to as optical fibers.

Known systems are designed so that light travels through an optical fiber by total internal reflection. Light entering the optical fiber is retained by and guided through the fiber, ultimately exiting at the other end. Basically, as light is propagated through the fiber, rather than escaping from the fiber, light striking the surface of the fiber is reflected. The extent of light reflection at the fiber surface, and conversely the loss of light from the fiber due to refraction, is a function of the indices of refraction of the fiber and its surrounding medium. For example, light incident on a high-to-low refractive index boundary (such as the interface between an optical fiber and air) at any angle greater than the critical angle is 100% reflected at the interface. Typical refractive indices for optical fibers range from about 1.2 to about 1.8, whereas the refractive index of air is 1.0003. The critical angle is a property of the light conducting material and defined as the smallest angle with the normal to the boundary at which total internal reflection occurs. Thus, for light propagated through a high-index material and striking the walls at greater than the critical angle, no refractive loss of light from the fiber occurs and the light is channeled through the fiber by total internal reflection.

In practice, despite the highly efficient transmission of light by total internal reflection in optical fibers, some light loss from the fiber inevitably occurs. Light losses may include, for example, refractive loss resulting from incident light striking the fiber walls at less than the critical angle. Additional losses may also be attributed to optical impurities present within the fiber, which may scatter or absorb light traveling through the fiber.

In addition to the light losses noted above, the attenuation of light intensity through an optical fiber may result from engagement of a fiber with a medium having a refractive index approaching the index of the fiber. For example, when an optical fiber is engaged by a liquid having a relatively high refractive index, such as water (refractive index 1.33) or gasoline (refractive index 1.38), light loss from the fiber may occur.

Using these principles, the detection of liquid levels by fiber optic sensing is well known. Numerous fiber optic devices and methods exist for the measurement of fluid levels, such as fuel in a storage tank. Many of these devices and methods take advantage of the attenuation of light intensity through a light-conducting medium by refractive loss as a consequence of engaging the optical fiber with a refractive medium such as a liquid.

Relying on this operating principal, U.S. Pat. No. 4,187,025 to Harmer discloses a light guide having alternating curvatures (e.g., S- or W-shaped light guides) to produce a light signal corresponding to the refractive index of a liquid in contact with the guide. When immersed in a liquid, the alternating curvatures of the light guide provide refractive passage of an amount of light that is variable and depends on the refractive index of the liquid. For these curvatures, the ratio of radius of curvature to the radius of the cylindrical light guide core is preferably between 3 and 5. The alternating curvature configuration of the device provides for enhanced sensitivity compared to a curved section bent in a single direction, such as the U-shaped device disclosed in U.S. Pat. No. 4,082,959 to Nakashima et al.

U.S. Pat. No. 4,287,427 to Scifres discloses several configurations of a fiber optical light guide useful for detecting liquids based on the various liquids' indices of refraction. The disclosed configurations include U-shaped and coiled light guides which, on immersion in a liquid, lose transmitted light as a function of the refractive index of the liquid.

A fiber optic detection system having a single fiber optic element in a U-shaped configuration and having a light variable loop section is disclosed in U.S. Pat. No. 5,362,971 to McMahon et al. Light transmitted through the light variable loop section escapes from the fiber when the loop section is contacted with a medium. For this system, the higher the index of refraction of the medium, the greater the amount of escaping light.

The devices noted above all share the characteristic of transmitting light through a smooth and continuous optical light guide. Optical guides having distinct reflective and refractive surfaces have also been employed to measure liquid levels. U.S. Pat. No. 3,995,169 to Odden discloses a U-shaped light pipe having planar internal reflecting surfaces positioned at both bends of the pipe. The planar surfaces act to reflect light from one arm of the pipe to the other arm without appreciable light loss when the refractive index of the surrounding medium is less than that of the light pipe. However, when the reflecting surfaces are immersed in a liquid, the planar surfaces become refractive surfaces and provide for the refraction of light from the light pipe to the surrounding liquid.

The use of reflective/refractive surfaces in optical devices to measure the presence of a liquid in contact with the surface, such as described above, is well known. Many of these optical devices include such surfaces present in conical configurations. In these optical devices, light is transmitted to the conical tip of the light guide where light is either: a) reflected across the tip and then returned via the light guide to a photodetector, when the conical tip of the guide is not in contact with a refracting medium such as a liquid; or b) refracted into the surrounding medium when the cone is immersed in a liquid. See, e.g., U.S. Pat. No. 3,384,885 to Forbush, U.S. Pat. No. 3,535,933 to Pliml, U.S. Pat. No.

3,553,666 to Melone, U.S. Pat. No. 3,683,196 to Obenhaus, and U.S. Pat. No. 3,8321,235 to Bouton et al.

In addition to the use of refractive surfaces in cone-shaped optical devices, refractive surfaces have also been incorporated into fiber optic sensors. A fiber optic probe system sensor having a refracting surface is disclosed in U.S. Pat. Nos. 4,851,817 and 5,005,005 to Brossia et al. The disclosed optical fiber has a U-shaped configuration similar to those noted above for Scifres and McMahon. However, in contrast to the above-noted optical fibers, the optical fiber in Brossia provides a sensor portion having a rough, abraded refracting surface in the light path. The abraded refracting surface provides an opportunity for light to refract from the fiber and into the sensed medium. The more abraded the fiber, the more opportunities for energy passing through the fiber to interact with the sensed medium.

The devices noted above use refractive light loss from a light guide to sense the presence of a refractive medium in contact with the guide. However, in addition to light loss from an optical fiber through refraction, light loss from a fiber may also occur through evanescent wave losses.

As used herein, the term "evanescent wave" refers to electromagnetic radiation that results from the propagation of light through a light-conducting medium, and that is present outside of the light-conducting medium. When light is transmitted through a high index of refraction medium the evanescent wave (or field) is produced in the adjacent lower index of refraction material and has intensity only within a fractional wavelength distance from the interface between the two mediums. The intensity of the evanescent wave decreases exponentially with distance from the fiber core (i.e., $E=E_o e^{-\alpha r}$ where E is the intensity of the evanescent wave, $E_o$ is the light intensity in the optical fiber, and $\alpha$ relates to the differences in the index of refraction of the two mediums, and r is the distance from the fiber core). The presence in the field of a medium that absorbs light of the wavelength of the transmitted light will result in light loss from the fiber.

Just as for refractive light loss from optical fibers, sensors and related methods have been devised to exploit evanescent wave loss from optical fibers as a means for measuring or monitoring, for example, liquid levels in a tank or reservoir. For example, U.S. Pat. No. 4,287,427 to Scifres describes a liquid-level monitor including a fiber optic light guide having a fiber consisting of a core material surrounded by a cladding material. While most of the guided light is confined to the core, a small amount of light is present in the cladding. If the cladding is removed or is sufficiently thin, the evanescent wave in the thin cladding or, in the absence of cladding, near the outer edge of the core interacts with the surrounding medium. Several configurations of the fiber optic light guide are disclosed including partially and fully cladded, coiled and U-shaped fibers. For this device, evanescent wave loss from the fiber occurs primarily when the wavelength of the guided light matches the absorbance wavelengths of the surrounding medium.

A fiber optic evanescent wave sensor system is described in U.S. Pat. No. 5,291,032 to Vali et al. The sensor system includes a light source, detector, and a cladded optical fiber having a reflector at one end. In the system, infrared light matching the absorbance wavelengths of hydrocarbons, such as those present in fuels, is transmitted into the fiber. The cladding layer is sufficiently thin to permit evanescent wave light loss to the environment. When the fiber is immersed in an absorbing medium, evanescent wave loss occurs as a function of the length of the fiber immersed in the liquid. The amount of light returned to the detector by reflection from the end of the fiber is indicative of the depth of fiber immersion and amount of liquid present.

Accordingly, despite the number and variety of optical fiber sensors and methods for sensing various environmental parameters, there remains a need in the art for improved optical sensors that are highly sensitive, low cost, durable, compact, portable and suitable for field installation. The present invention seeks to fulfill these needs and provides further related advantages.

SUMMARY OF THE INVENTION

Briefly, the present invention provides an optical sensor that uses an optical fiber to detect the presence of a medium present in a sensed environment. The sensor produces a signal corresponding to the amount of evanescent wave light loss from the optical fiber to an absorbing medium in contact with the fiber.

In one aspect, the present invention provides an optical sensor comprising a light source, a light detector and signal generator, and an optical fiber extending between the light source and detector. The optical fiber includes a sensing length comprising a return bend in the fiber, where the return bend has a bend radius less than or equal to 2.5 times the radius of the optical fiber. In a preferred embodiment, the bend radius is less than or equal to twice the radius of the optical fiber. In one embodiment, the sensing length of the sensor's optical fiber further includes a planar sensing surface. In a preferred embodiment, the planar sensing surface has a maximum length of about twice the radius of the return bend.

In another embodiment, the optical sensor further includes a signal processor for output signaling, and for indicating the detection of a medium in the environment.

In yet another embodiment, the optical sensor includes a beamsplitter positioned between the light source and the sensing length to provide electronic feedback to the light source supply to control and regulate its emission.

In still another embodiment, the optical sensor includes an analyte-specific coating on the fiber's sensing length.

In another aspect of the present invention, a method is provided for detecting the presence of a medium in an environment comprising contacting the sensing length of the optical sensor of this invention with the medium. The method of the present invention is useful in detecting the presence of any medium in contact with the sensor's sensing length that absorbs light at the wavelength or wavelengths emitted by the sensor's light source. The method of this invention is particularly useful in detecting the presence of water, hydrocarbons, hydrocarbons in water.

In a further aspect, the present invention provides a sensing system that includes a sensor capable of detecting and signaling the presence of fluid in an enclosure. The system, which may be installed or incorporated within electronics and communications enclosures that house fluid-sensitive components, is useful in the early detection and warning of fluid leaks into such enclosures. In addition to a sensor, the system may include a means for conducting fluids entering the enclosure to the sensor, and absorbent material to absorb any entering fluid.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

In one aspect, the present invention provides an optical sensor that uses an optical fiber carrying an evanescent wave associated with an internal beam of light. The sensor produces a signal corresponding to the amount of evanescent wave light loss to a medium present in the sensed environment. In another aspect of the present invention, a method for sensing a medium present in a sensed environment is provided.

As used herein, the term "medium" refers to any substance, the presence of which may be detected by the sensor of the present invention. Generally, the medium may be a any fluid, including a gas or liquid, that absorbs light at the wavelength(s) emitted by the sensor's light source. In certain instances, the medium may also be a solid having absorbance properties as noted above.

The term "sensed environment" refers generally to the environment surrounding the sensor of the present invention and includes any medium, as defined above, in contact with the sensor's sensing length and/or sensing surface.

The terms "amount of light" and "intensity of light" are used interchangeably and refer to the number of photons that, for example, are generated by the light source, travel through the optical fiber, are present in the evanescent wave, and are received at the light detector.

Figure 1:
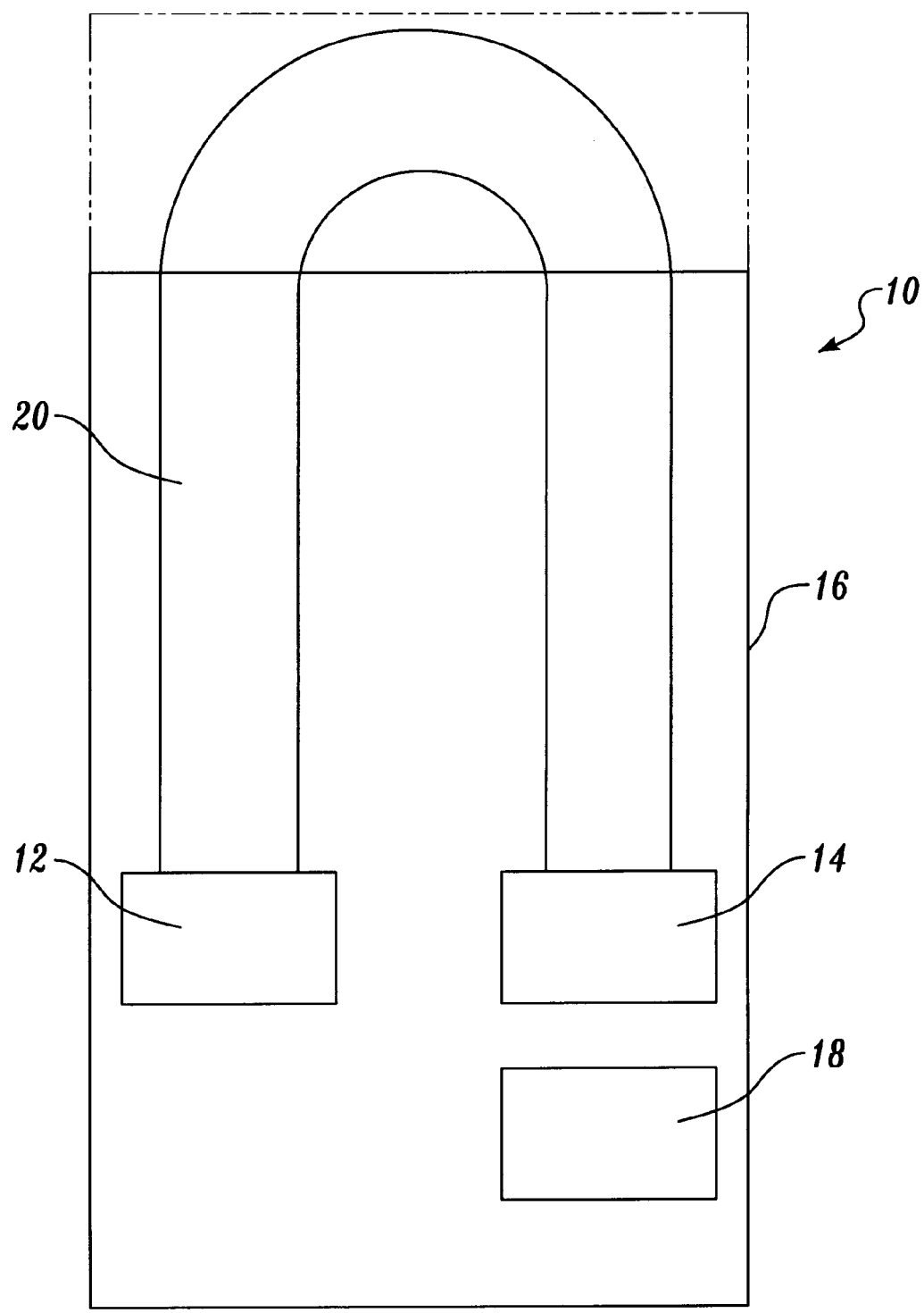
FIG. 1 is a schematic representation of an optical sensor of the present invention.

In general, as illustrated in FIG. 1, a first embodiment of the invention provides a optical sensor 10 having a light source 12 for generating light, a light detector and signal generator 14 for receiving light and generating variable signals dependent on the amount of light received, and an optical fiber 20 extending between the light source to the light detector and signal generator. The sensor includes a housing 16 to facilitate the convenient incorporation of the sensor into an environment, and a signal processor 18 connected to the light detector and signal generator for output signaling and indicating the detection of a medium in the sensed environment.

In operation, light is transmitted from the light source 12 through the optical fiber to the light detector 14 where a variable signal is generated depending on the amount of light received at the detector. In the absence of a light absorbing medium in the sensed environment, the amount of light received at the detector will be substantially the amount of light that is generated by the light source. In contrast, when a light-absorbing medium is present in the sensed environment, light transmission through the fiber will be attenuated, and the amount of light received at the detector will be the difference between the amount of light generated by the light source and the amount of light absorbed by the medium in the sensed environment. The greater the amount of light absorbed by the medium, the less the amount of light received at the detector.

Figure 2A:
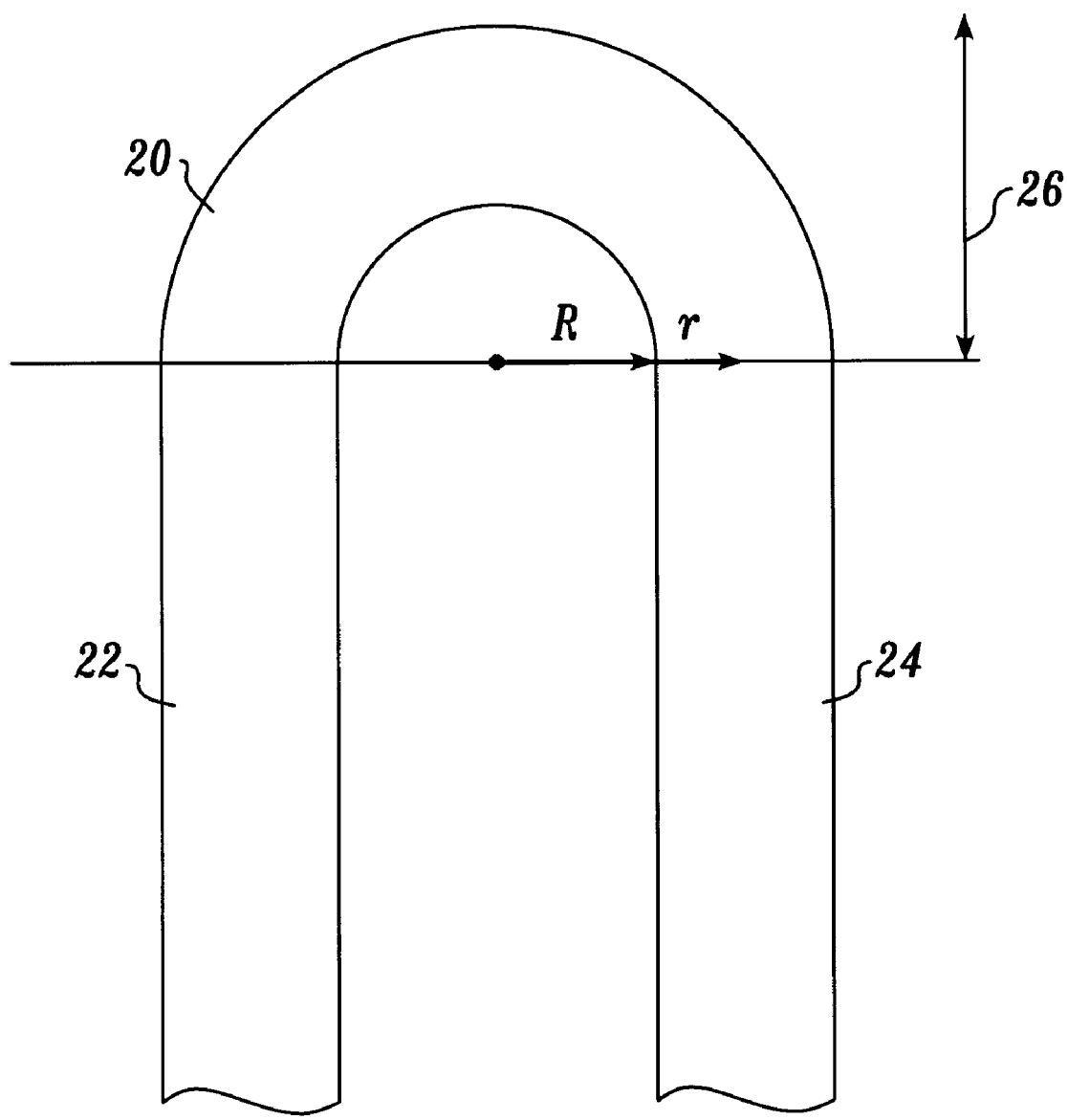
FIGS. 2A and 2B are schematic representations of portions of the optical sensor of the present invention.

Referring now to FIG. 2A, the optical fiber 20 of the optical sensor of the present invention has, in general, a return bend or U-shaped configuration that provides a guide for the light generated by the source and received at the detector. The optical fiber has a sensing length 26 that provides for the passage of light by evanescent wave into a medium in contact with the sensing length. Light generated by the source is guided through input arm 22 of the fiber to sensing length 26, and on to the detector through output arm 24. The sensing length of the optical fiber includes the return bend portion of the fiber. In a preferred embodiment, the sensing length comprises a sharp return bend (e.g., 180°) in the fiber having a bend radius R, defined as half the distance between input arm 22 and output arm 24 as indicated in FIG. 2A, that is less than or equal to 2.5 times the radius r of the optical fiber core (i.e., $R/r \leq 2.5$). In a particularly preferred embodiment, the bend radius R is less than or equal to twice the radius r of the optical fiber core (i.e., $R/r \leq 2.0$).

Figure 2B:
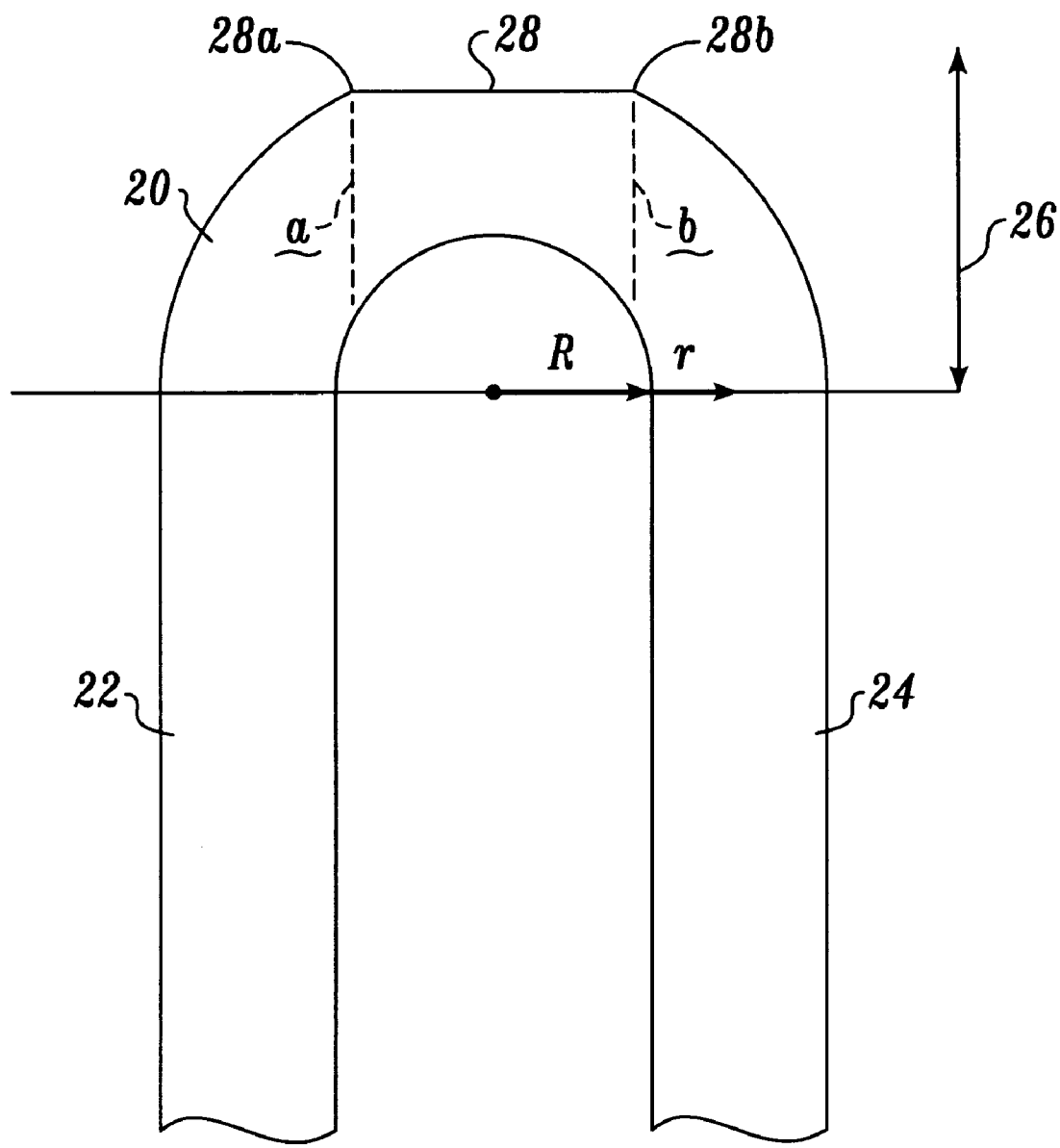

In another embodiment of the optical sensor of this invention, the sensor's sensing length further includes a planar sensing surface. Referring to FIG. 2B, the sensing surface 28 is located at the apex formed by the return bend in the optical fiber. A medium in contact with the sensor's sensing length and/or the sensing surface and capable of absorbing light at the wavelength(s) emitted by the light source can be detected by the optical sensor of this invention.

The sensing surface of the optical fiber is a planar optical surface. The sensing surface may be prepared by micromachining the apex of a return bent optical fiber to provide such a planar and smooth (i.e., optical) surface. As noted above, the optical sensor of this invention operates on the principal of evanescent wave sensing and, as such, the sensing surface is not a refraction/reflection surface. Rather, the planar optical surface of the sensing surface is smooth and free from grooves and/or other aberrations including striations to minimize refractive loss from the fiber. The smooth, nonrefractive sensing surface is also located at the apex of the optical fiber bend so as to further minimize refraction of light from the fiber. The positioning of the sensing surface is such that, unlike the refracting/reflecting surfaces of the prior art devices noted above, the sensing surface does not extend to the outer periphery of the bend where refraction may readily occur. Thus, to minimize direct refractive light loss from the fiber, the sensing surface is centered at the apex of the return bend and has one end 28a substantially aligned with the innermost edge of the light path of the input arm 22 and the other end 28b substantially aligned with the innermost edge of the light path of the output arm 24. In a preferred embodiment, the sensing surface is centered at the apex of the return bend of the fiber and has a maximum length of about 2R. The position and length of a sensing surface having a length of about 2R, noted by dashed vertical lines designated a and b, is shown in FIG. 2B.

As noted above, the sensing surface has a maximum length of about 2R, and optical sensors of the present invention include sensors having sensing surface lengths less than 2R. The length of the sensing surface may be varied depending on the sensing application. In general, the greater the length of the sensing surface, the greater the sensitivity of the optical sensor. Preferably, the length of the sensing surface is between about R and 2R. It will be appreciated that as the length of the sensing surface decreases and approaches zero as the lower limit, the sensing surface becomes a point, and the sensing length of the sensor of the invention comprises a smooth return bend. Accordingly, in addition to optical sensors that include sensing surfaces having lengths up to 2R, optical sensors having diminishingly small sensing surfaces, such as those having a sensing length comprising a smooth return bend, are also within the scope of the present invention. Nevertheless, a planar sensing surface of substantial length is preferred.

It can be demonstrated that the sensitivity of the optical sensor of this invention is attributable to the sharpness of the fiber's return bend. It can also be demonstrated that the planar sensing surface further enhances the sensor's sensitivity. Although not presented or intended to limit the scope of the invention, it is believed that the sharpness of the fiber's bend optimizes the evanescent wave present in this portion of the fiber, and that the planar sensing surface coupled with the fiber's sharp return bend further optimizes the evanescent wave. It is believed that the sharp return bend tends to concentrate the density of multimode reflections normal to the tangent of the apex (i.e., increase the number of reflections per unit distance along the fiber) which has the effect of creating a continuous evanescent wave (or evanescent field) along fiber's return bend apex and, when present, the planar sensing surface. Accordingly, by virtue of its shape and configuration, the optical fiber of the present invention is particularly well-suited to generating an enhanced evanescent surface wave thereby probing a medium in contact with the sensing length and/or sensing surface. In fact, the high sensitivity of the optical sensor of the present invention is a direct result from the fiber's shape and configuration. Variations in the dimensions of the sensing surface may be made to achieve the detection and quantitation of specific media.

The performance characteristics of the optical sensors of the present invention are described and summarized in Examples 2 and 3. In Examples 2 and 3, the characteristics of the optical sensors of this invention having R/r≦2.5 and sensing lengths comprising either a smooth return bend or a planar sensing surface are compared to various other devices including sensors incorporating straight fibers and bent fibers having bend radii greater than 2.5. Example 2 describes the performance characteristics of representative sensors in the detection of water, and the detection of oil in water is described in Example 3.

The optical fiber useful in the present invention is made of a light conducting material. A number of suitable fibers are commercially available from a variety of manufacturers including Mitsubishi Cable Co., AT&T, Belden, SIECOR, and Spectran. In the context of the present invention, the optical fiber includes a fiber core made of a light conducting material and, optionally, a cladding material surrounding the fiber core. For embodiments of the optical sensors of this invention that employ cladded optical fibers, the cladding is removed from the fiber in the region of the sensing length. Light conducting materials include any materials capable of conveying light by multiple internal reflections. Suitable materials include plastic materials, such as polystyrene, polyacrylate, and polymethylmethacrylate materials, and glass materials such as quartz, silica glass, borosilicate glass, lead glass, and fluoride glass materials. Preferred optical fibers include plastic fibers having diameters from about 250 to about 2000 $\mu$m, and glass fibers having diameters from about 50 to about 250 $\mu$m. Suitable optical fibers are essentially transparent to the wavelength(s) of light generated by the light source, may be either single or multimode fibers, and may include fibers having specific transmission modes and wavelength bands. In a preferred embodiment, the optical fiber is a multimode plastic fiber having a diameter of 1000 $\mu$m, such as commercially available from Mitsubishi Cable America, Inc., New York, N.Y. (Eska™).

The light source of the optical sensor serves to generate light, and may be selected based on the sensing application where the source's output wavelength is matched with the wavelength of absorbance of the medium to be sensed. In a preferred embodiment, the light source emits light at a wavelength or wavelengths in the red and/or near-infrared region of the spectrum, i.e., from about 600 to about 1500 nm. In general, light sources useful in the optical sensor of this invention include tungsten light sources, light-emitting diodes, and laser diodes. Suitable laser diodes include diodes composed of gallium arsenide (GaAs) and aluminum gallium arsenide (AlGaAs) materials, which are electroluminescent and emit in the near-infrared (i.e., 1050 and 1150 nm, respectively). Other suitable light sources include light-emitting diodes having peak emission wavelengths at, for example, 850 nm, 880 nm, 940 nm (available from Clairex Technologies, Plano, Tex., as models CLC216PR, CLC211PR, and CLC112PR, respectively), 950 nm, and 1300 nm (available from Siemens Optoelectronics, Inc., as models SFH450 and STL51007G, respectively). In a preferred embodiment, the light source is a light-emitting diode having a wavelength of emission centered at about 950 nm, commercially available from Siemens Optoelectronics, Inc.

The light detector and signal generator of the optical sensor receives light from the light source and generates variable signals dependent on the amount of light received at the detector. Suitable light detectors include any photodetector, such as a photodiode or phototransistor, capable of responding to light emitted from the light source. Preferably, the light detector has a photosensitivity (i.e., photoresponse) over at least the bandwidth of the source's emission wavelengths. Light detectors useful in the optical sensor of this invention include, for example, models SFH350 and the SRD0021x series photodetectors commercially available from Siemens Optoelectronics Inc., and models CLC400 CLC600 series photodetectors available from Clairex Technologies. In a preferred embodiment, the light detector is a phototransistor, such as model SFH350, commercially available from Siemens Optoelectronics Inc. As noted above, the optical sensor may also include a signal processor connected to the light detector and signal generator to process and output signals from the signal generator to indicate the presence of a selected medium in the environment.

Figure 3A:
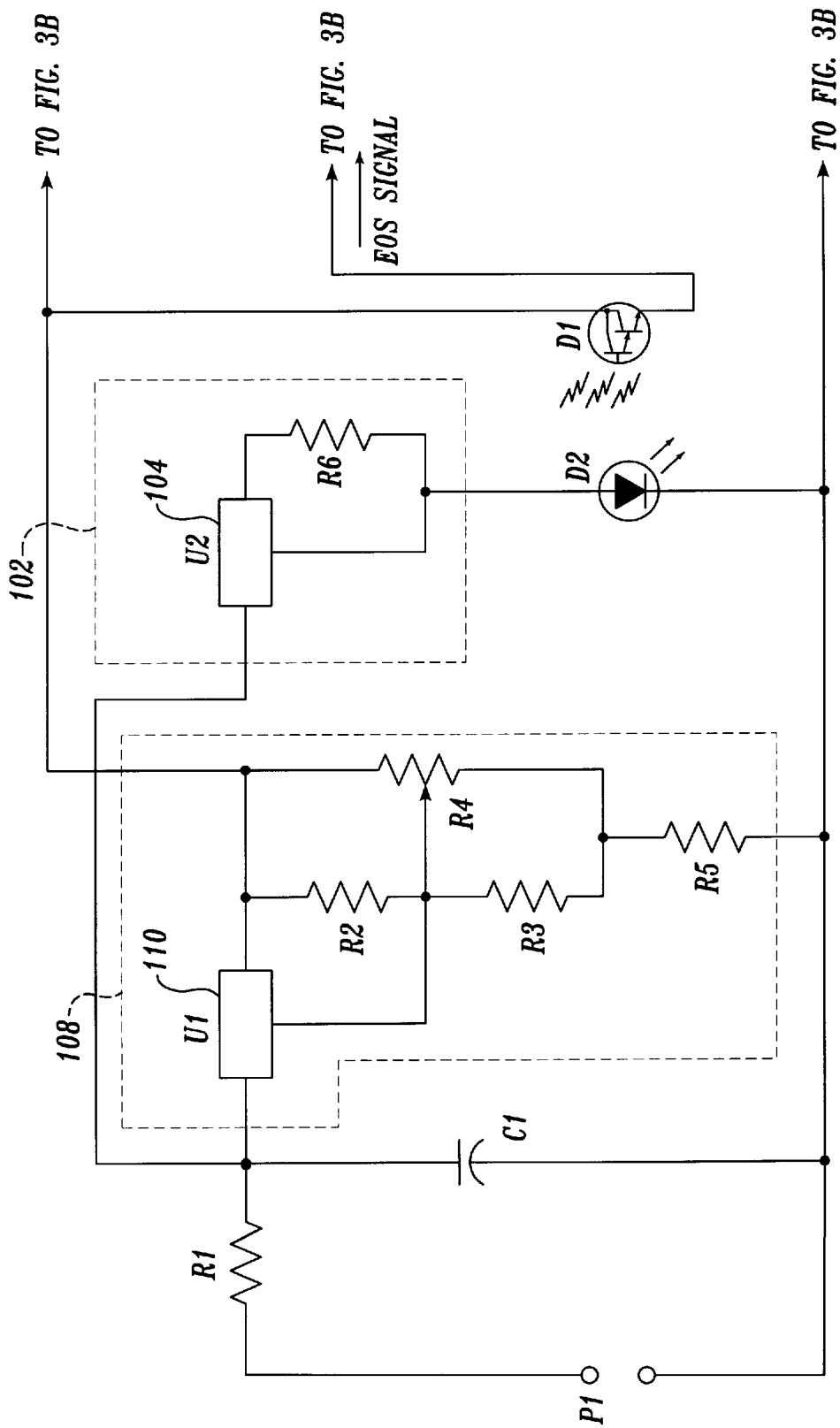
FIGS. 3A and 3B are circuit diagrams for a representative optical sensor of the present invention.
Figure 3B:
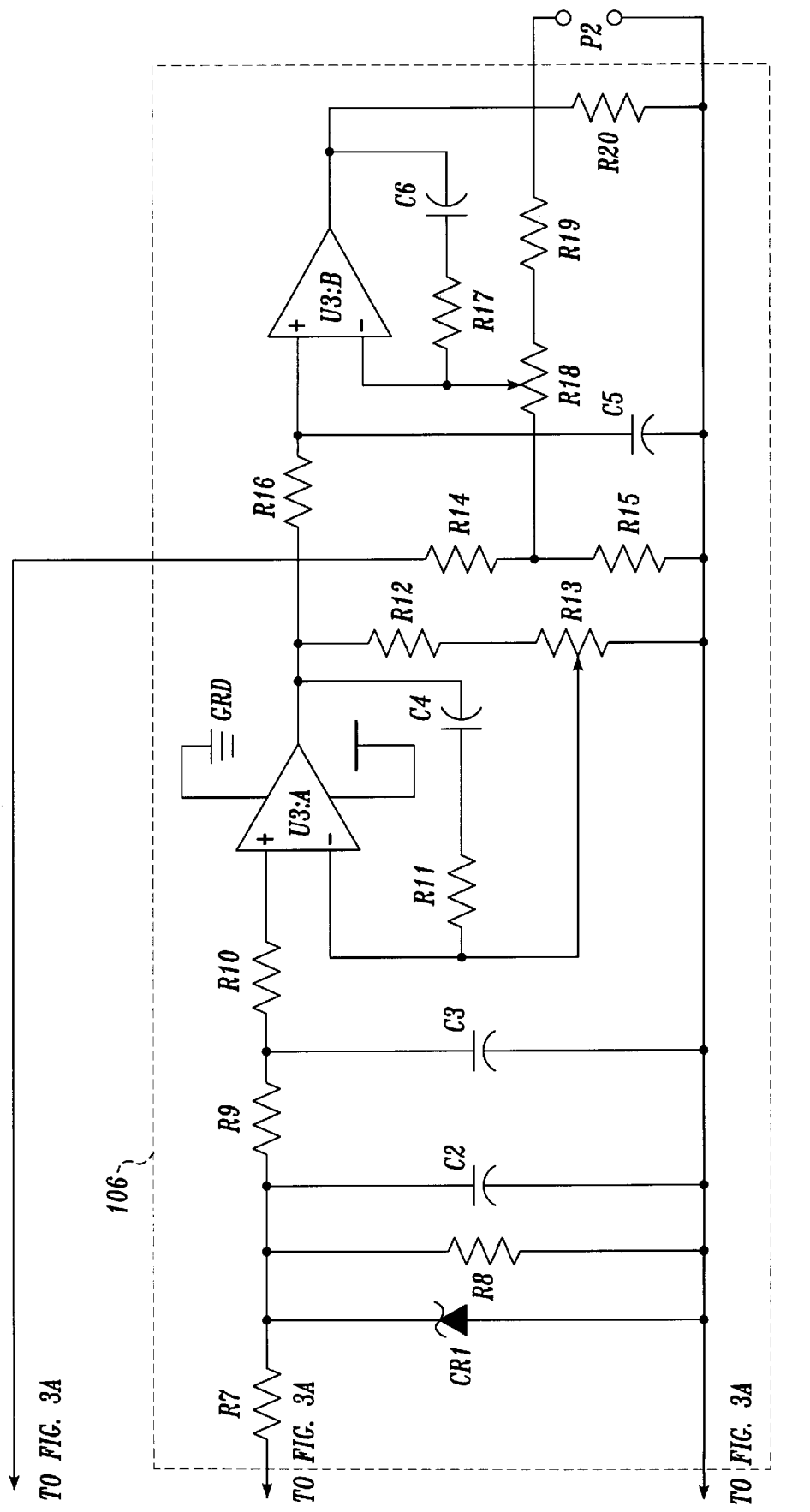

The electronic components of a representative optical sensor of this invention are shown in the circuit diagrams of FIGS. 3A and 3B. With reference to FIGS. 3A and 3B, power for the light emitting diode D2 can be provided by a constant current source 102 based on a three terminal adjustable regulator 104, such as a National Semiconductor LM317LZ. Regulator 104, in turn, receives input power (12 volts DC) through an input filter R1, C1. For the photodetector D1 and the signal processing circuit 106, power is supplied by a voltage source 108 which also can be based on a three terminal adjustable regulator 110 (LM317LZ) receiving power (12 volts DC) through the input filter R1, C1. The output from the photodetector is applied to a voltage divider R7, R8, with the maximum voltage across resistor R8 limited by a Zener diode CR1. The voltage across resistor R8 is filtered by a two-stage filter R9, C2 and R10, C3, before being amplified by a chopper-stabilized operational amplifier circuit (U3:A). The processing circuit then subtracts a reference voltage (found at the junction of R14 and R15) from the amplified voltage, and further amplifies the voltage difference at another operational amplifier (U3:B). This amplified, offset voltage is the output.

The optical sensor may include a housing to form a sensor module to facilitate the convenient incorporation of the sensor into an environment. The housing for the optical sensor may take any one of a variety of forms depending on the sensing application. For example, the housing may be a cylindrical sleeve of plastic and/or metal that surrounds the optical fiber and seals the light source and detector, as well as the signal generator and processor, from the sensed environment. In the sensor module, the sensing length of the optical fiber is exposed to the environment for sensing of a selected medium. Alternately, the housing may be a sensor sleeve, such as described above, further including a threaded surface such that the sensor may be inserted and secured into an environment by a threaded sensor receiving means. Representative sensor modules are illustrated in FIGS. 4A and 4C.

The housing used to form the sensor module may, under certain circumstances, impose the bend radius in the optical fiber useful in the sensor of the present invention. For example, in one embodiment, the sensor module housing is a cylindrical sleeve having an outer diameter of about 0.2 inches (with a nominal wall thickness of about 0.02 inches). The use of a 1000 $\mu$m (0.04 inch) diameter optical fiber in a return bend configuration with such a housing results in a separation of about 0.08 inches (R=0.04 inch) between the input and output arms of the fiber. In such a configuration, the bend radius R (0.04 inch) is equal to twice the fiber radius r (0.02 inch), i.e., R/r=2.0. Such a configuration is distinguished from the configurations of the prior art sensors noted above that contain bent optical fibers having R/r>>2.

Figure 4A:
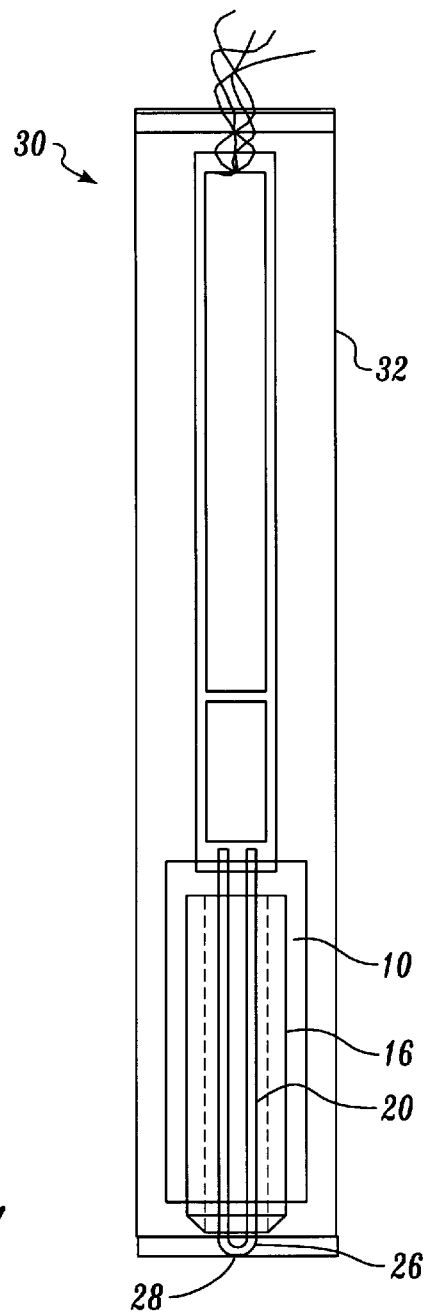
FIGS. 4A and 4C are diagrammatic side elevations of sensor modules of an optical sensor of the present invention.
Figure 4B:
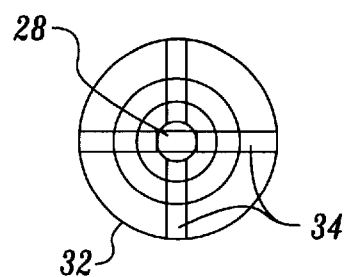
FIG. 4B is a diagrammatic end elevation of the sensor module shown in FIG. 4A.
Figure 4C:
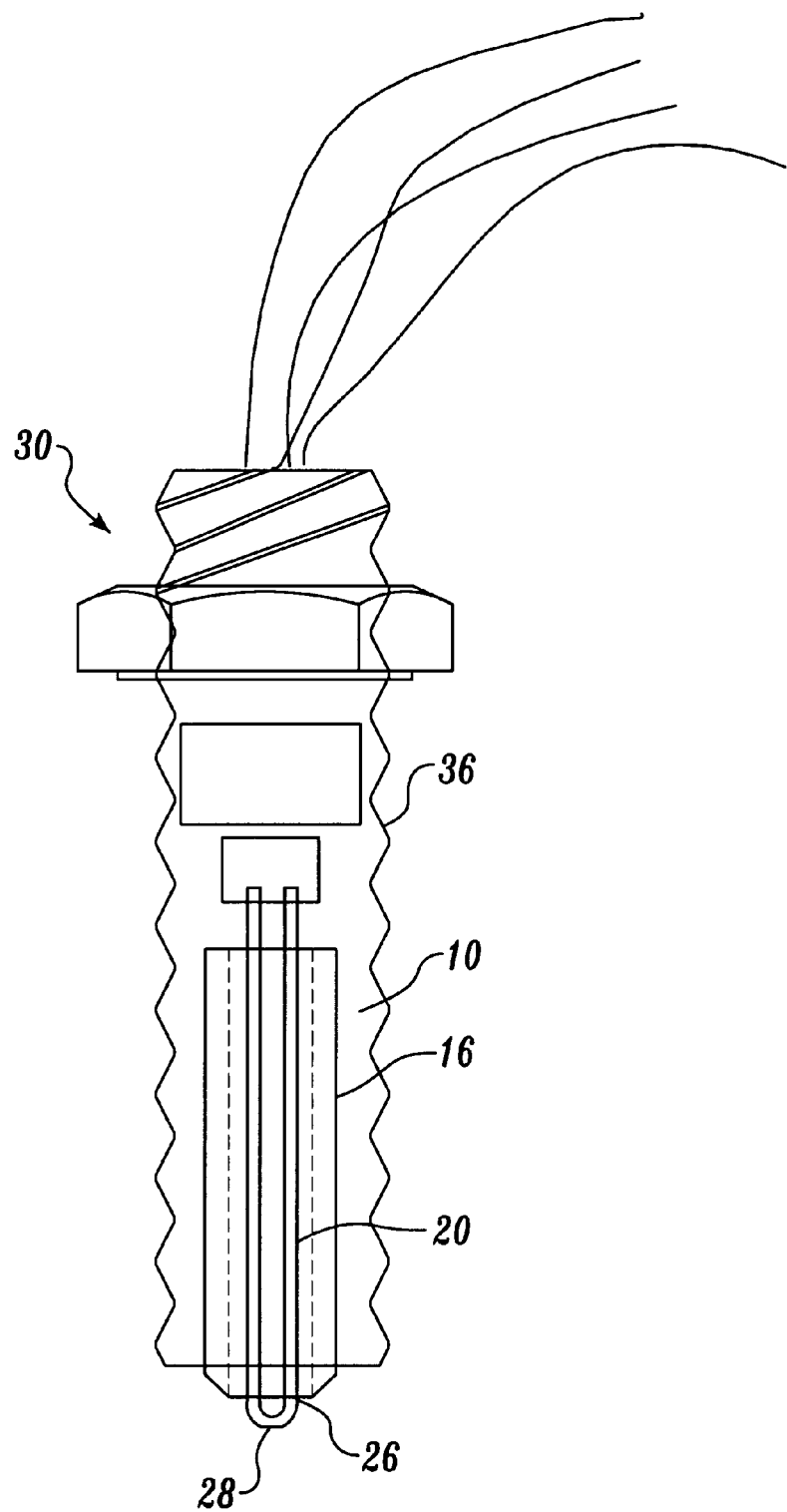

Referring to FIG. 4A, in one embodiment the sensor module 30 has a cylindrical body 32 that encompasses optical sensor 10. In this embodiment, the input and output arms of optical fiber 20 are enclosed in housing 16, and sensing length 26, including optional sensing surface 28, extend from the housing to permit engagement of the sensing surface with a medium present in the sensed environment. In an embodiment of this sensor module, the cylindrical body 32 extends to a length of at least the outer reach of sensing length 26 and optional sensing surface 28, and further provides channels 34 in cylindrical body 32 as a means for permitting the engagement of a medium with a sensing surface 28. An end elevation of the sensing end of the sensor module depicting sensing surface 28 and channels 34 is shown in FIG. 4B. A sensor module 30 having a threaded body 36 that encompasses optical sensor 10 is shown in FIG. 4C. As noted above for the sensor module having a cylindrical body, sensing length 26 and optional sensing surface 28 may either extend from or be recessed in threaded body 36. In embodiments having a recessed sensing surface, the threaded body may include channels for the engagement of a medium with the sensing surface.

Figure 5B:
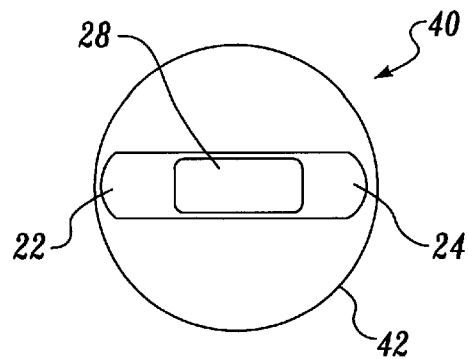
FIG. 5B is a diagrammatic end elevation of the molded sensor shown in FIG. 5A.
Figure 5A:
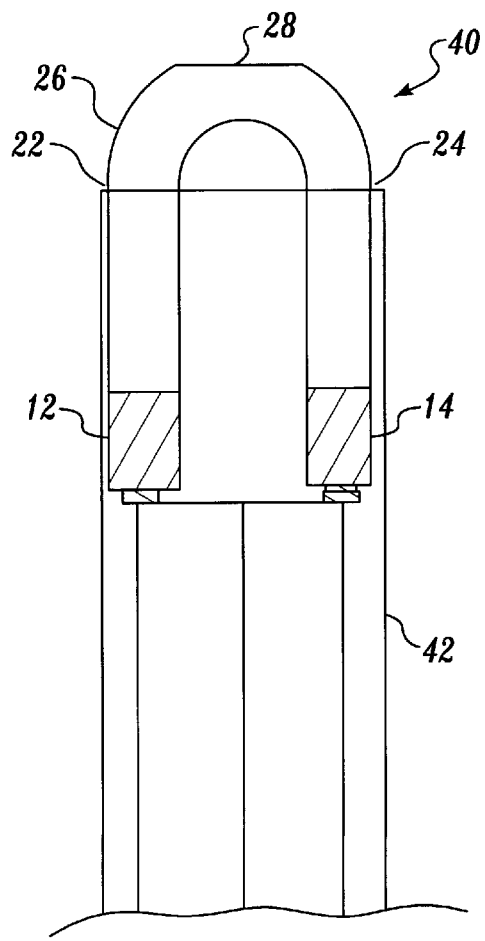
FIG. 5A is a diagrammatic side elevation of a representative molded sensor of the present invention.

In a preferred embodiment, the optical sensor of the present invention is a molded sensor made of a plastic light conducting material such as polymethyl methacrylate. The molded sensor includes the optical sensor components noted above (e.g., the light guide having a sensing length, the light source, and the light detector) where the source and detector are fitted into the plastic mold. A representative molded sensor is illustrated in FIG. 5A. Referring to FIG. 5A, the light source 12 and light detector and signal generator 14 of molded sensor 40 are located in cylindrical body 42 of the molded sensor. Extending from the cylindrical body 42 are input arm 22, sensing length 26 including sensing surface 28, and output arm 24. An end elevation of the molded sensor is shown in FIG. 5B.

The molded sensor offers the advantage of ease of production including the uniform manufacture of the return bend and, optionally, the planar optical surface of the fiber's sensing length. An additional advantage of the molded sensor is that no leakage of liquid from the environment into the sensor can occur.

Figure 6:
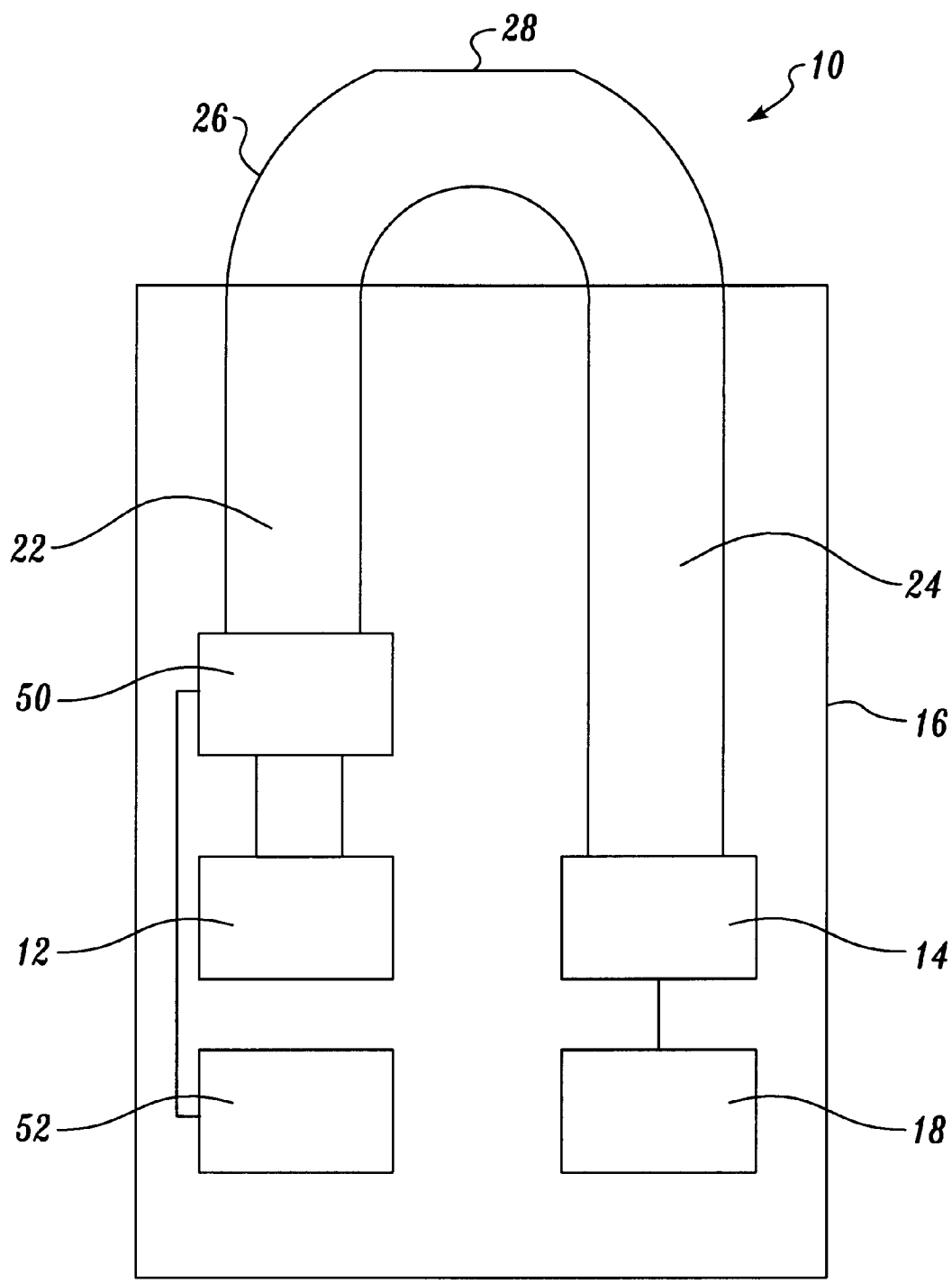
FIG. 6 is a schematic representation of an optical sensor of the present invention that includes a beamsplitter.

In one embodiment, the optical sensor includes a beamsplitter positioned in the path of the light generated by the source. Referring to FIG. 6, in one embodiment the sensor has beamsplitter 50 positioned along input arm 22 between light source 12 and sensing length 26. The beamsplitter directs a portion of the generated light to a second light detector and signal generator 52 such that the intensity of the light generated by the source may be monitored. The beamsplitter and associated second light detector and signal generator provide a means for calibrating the intensity of the source and allow for the quantitation of the amount of light loss from the sensing length of the optical fiber by comparing the amount of light received at light detector 14 and the second light detector.

Alternatively, a phototransistor may be positioned directly along input arm 22 to provide electronic feedback to the light source supply to control and regulate the intensity of the light emitted from the source.

The optical sensor of the present invention may be employed in a number of configurations and sensing environments to monitor and report conditions and changes in conditions measurable by the sensor. As noted above, to best sense the presence of a particular medium, the sensor's light source emission wavelength or wavelengths should overlap to at least some extent with the absorbance wavelengths of the medium sought to be detected. In the context of the present invention, sensors having light sources emitting red and near-infrared wavelengths are particularly useful in detecting the presence of water and hydrocarbons such as fuels including gasoline and oil. As used herein, the term "hydrocarbon" refers to a substantially organic compound that includes carbon-hydrogen (i.e., C—H) bonds.

The sensor of the present invention may be located in certain environments where, for example, the presence of water may be hazardous to the smooth functioning of certain components such as electrical components present in an electrical box. In such an application, a sensor may be installed in the box in such a position that any water that finds its way into the box ends up in contact with the sensing length and/or sensing surface of the sensor. In the event that water does collect and contacts the sensing length and/or sensing surface, the attenuation of light through the optical fiber of the sensor accompanying the contact of water results in the generation of an output signal indicating the presence of water in the electrical box. Notice of the presence of water in the box allows for action to be taken to service the particular box and avoid any costly damage that would result from unnoticed and unattended accumulation of water in the box.

Thus, in another aspect, the present invention provides a sensor system that includes a sensor capable of detecting and signaling the presence of fluid in an enclosure. The system can be integrally formed with or installed within an enclosure that contains one or more fluid-sensitive components including, for example, electronic and communications connections or splices. In accordance with the sensor system, fluid entering the enclosure is conducted to the sensor which detects the presence of the fluid and transmits a signal via a communications line to a communications control center. Upon receipt of this information, action may be taken to service the enclosure and thereby prevent damage to the fluid-sensitive component(s) housed within the enclosure. Because the sensor generates a signal in advance of fluid entering that portion of the enclosure housing the fluid-sensitive component(s), a prompt response to the sensor's signal can avoid costly damage to the enclosed components.

The sensor system of the present invention is particularly useful in connection with splice closure systems. The term "splice closure system" generally refers to a device that encloses electronic and/or communication cable splices (i.e., connections) including fiber optic splices, mechanical and fusion splices, which are useful in a variety of applications including aerial, building, direct buried and underground applications. Splice closure systems are well known in the art and may take any one of a number of forms or configurations. Generally, splice closure systems are designed to protect sensitive electronic and communication splices from damage that may otherwise result from exposure to hostile environmental conditions including temperature extremes, sunlight, wind, and precipitation such as rain, sleet, and snow. Among other protections, these closure systems seek to prevent moisture from entering the closure and causing damage to the water-sensitive components contained within the enclosure. The sensor system of the present invention can be incorporated into a splice closure system to provide a means for monitoring moisture within such a closure.

As noted above, the sensor system can be integrally formed with or installed within an enclosure that houses fluid-sensitive components. The sensor is preferably incorporated into the enclosure in a position such that a fluid entering the enclosure contacts the sensor prior to traveling to and potentially damaging the enclosure's fluid-sensitive component(s). In addition to the sensor, the system preferably includes a means for conducting any fluid entering the enclosure to the sensor and an absorbent material to absorb any fluid entering the enclosure.

Figure 10:
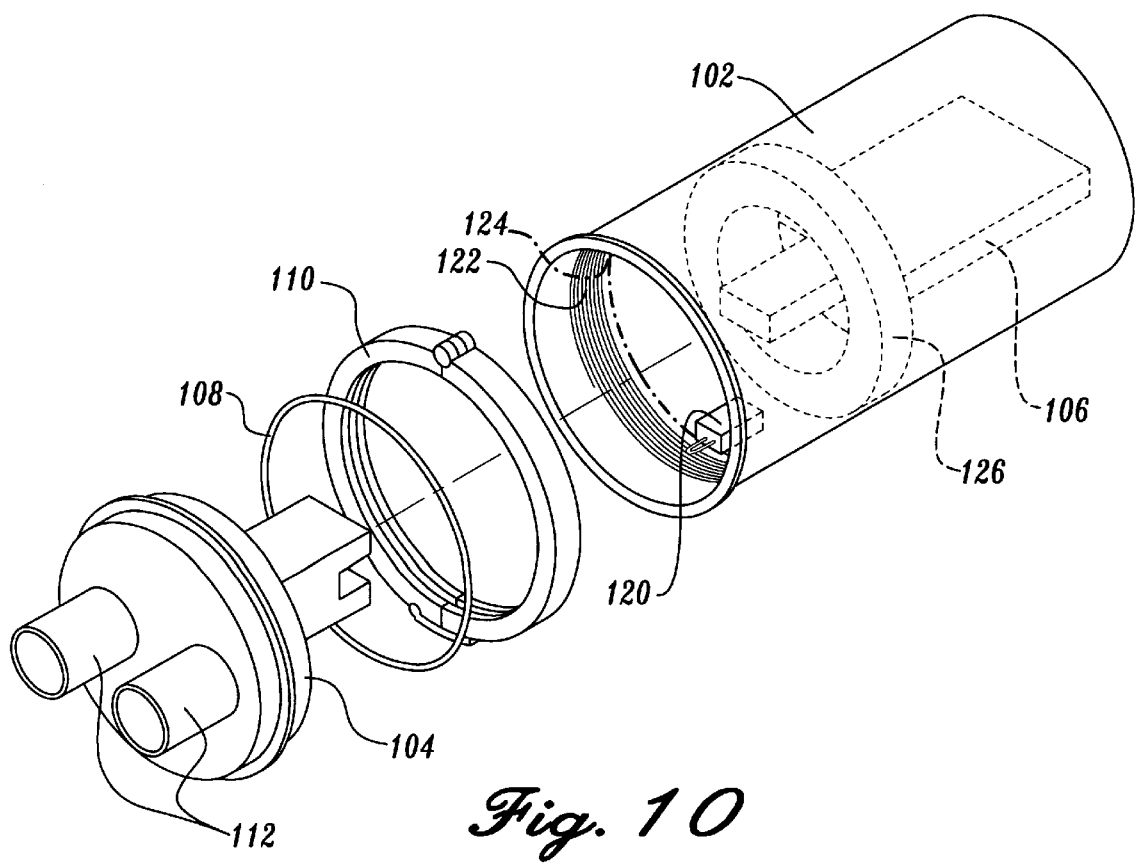
FIG. 10 is a schematic representation of a sensor system of the present invention.

A schematic illustration of a representative sensor system associated with a typical enclosure for housing fluid-sensitive components (i.e., a splice closure system) is shown in FIG. 10. The splice closure system depicted in FIG. 10 is a common closure configuration having input and output cables extending from one end of the closure. It will be appreciated that other closure configurations, including closures having input and output cables extending from opposite ends of the closure, are within the scope of the present invention and would benefit from the advantages afforded by sensor system of this invention. In such an embodiment, the closure can include two sensor systems, corresponding to each cable port, located near each end of the closure. It will also be appreciated that, depending on the particular closure system, the closure can include any one of a variety of means for securing and sealing the closure's cover to the closure's base. One such means, a clamp and O-ring seal, is illustrated in FIG. 10.

Referring to FIG. 10, the illustrated splice closure system generally includes base 102, dome 104, splice organizer tray 106, O-ring seal 108, and clamp 110. Clamp 110 secures dome 104 to base 102 and provides a seal through O-ring 108. The O-ring forming the dome/base seal is preferably made from a water impervious elastomeric material. Dome 104 further includes ports 112 for receiving input (i.e., feeder) and output (i.e., distribution) cables. The cables are organized and spliced in the closure on tray 106.

As shown in FIG. 10, the representative sensor system includes sensor 120, a fluid conducting means 122 (or 124 shown in broken line), and absorbent barrier 126. In a typical splice closure system, the sensor is powered from a source associated with either the input and/or output cables, and the sensor signals the presence of fluid in the closure through a communication line, for example, optical fibers associated with the cables noted above.

The sensor is generally positioned between the closure's primary seal and the closure's fluid-sensitive components. Referring again to FIG. 10, when dome 104 is secured to base 102, sensor 120 is positioned between O-ring 108 and absorbent barrier 126. In the embodiment illustrated in FIG. 10, absorbent barrier 126 is a ring-shaped barrier in communication with the interior surface of base 102 and having an aperture of size sufficient to permit tray 106 to pass unimpeded into the closure's base. Barrier 126 is a continuous ring mounted in the closure base and includes an absorbent material, preferably a superabsorbent polymeric material. In its sealed configuration, absorbent barrier 126 is positioned between sensor 120 and the closure's fluid-sensitive components located on tray 106. As a result of this configuration, any fluid entering the closure through the dome/base connection is first directed by a conducting means to the sensor, where it is detected and its presence signalled. Any fluid migrating beyond the sensor and toward the fluid-sensitive component located on tray 106 is intercepted and absorbed by the absorbent barrier. Thus, barrier 126 provides the closure with a measure of protection during the period of time between the sensor's initial signaling of the presence of fluid in the closure and servicing of the closure.

Suitable sensors useful in the system of the present invention include any sensor capable of detecting and signaling the presence of a fluid, for example, water or moisture. Preferably, the sensor is an optical sensor such as a sensor of the present invention described above.

Generally, the sensor is positioned in the enclosure to be sensed such that any fluid that enters the enclosure collects at or near the sensor for ready detection. Accordingly, the sensor is generally positioned at the enclosure's lowest point, for example, at the lowest point of the enclosure's floor. The fluid conducting means can include any one of a number of means including, for example, a fluid conduit and other routing means. As shown in FIG. 10, a preferred means for conducting a fluid to the sensor is helical groove 122 (i.e., a "racetrack"), which encircles the interior circumference of base 102 between O-ring 108 and sensor 120. In another preferred embodiment, the fluid conducting means is flange 124 extending inwardly from the interior surface of base 102 and in communication with sensor 120. Fluid entering the closure and travelling toward the sensor encounters flange 124 and is conducted to the sensor.

Figure 7A:
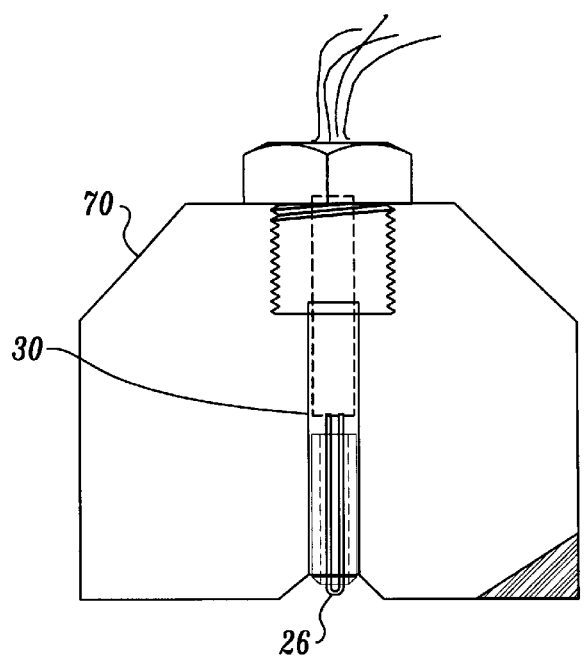
FIGS. 7A and 7B are diagrammatic side elevations of representative embodiments of sensor packages in accordance with the present invention.

Employing the advantages offered by the sensor of the present invention with regard to the sensor's ability to detect the presence of hydrocarbons such as fuels in water, the sensor may be incorporated into a sensor package, such as a flotation device, and located in bodies of water (e.g., rivers, streams, ponds, and lakes) to detect fuel spills. An example of such an embodiment is illustrated in FIG. 7A. Referring to FIG. 7A, sensor module 30 is positioned in a flotation device 70 made of buoyant material. Flotation device 70 is designed to float on a liquid surface and permit contact of sensing length 26 and/or sensing surface 28 with the surface of the liquid.

Figure 7B:
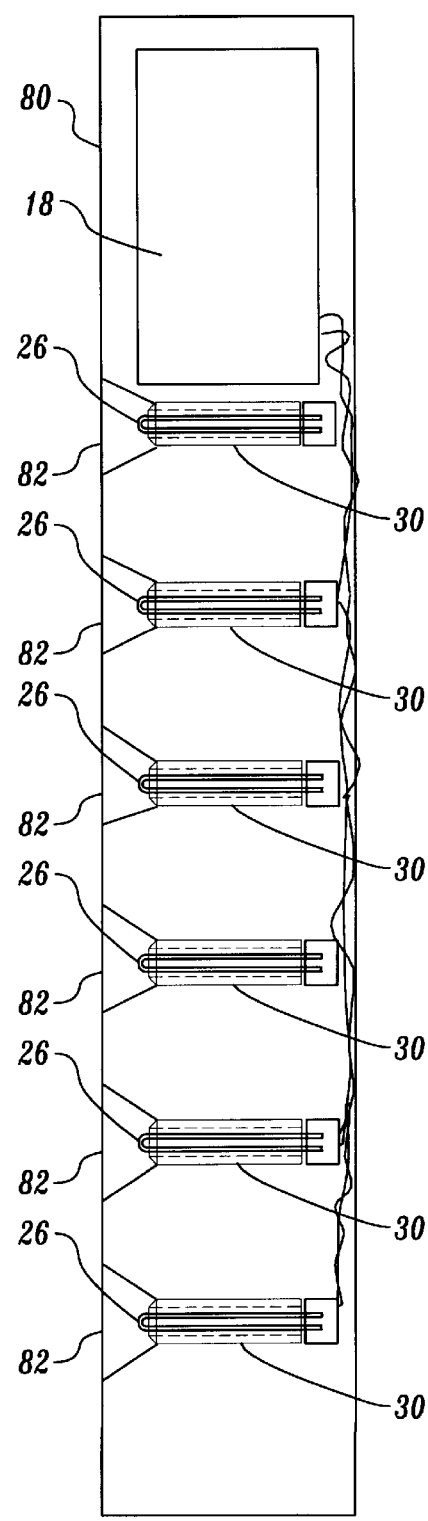

The sensor of the present invention may also be incorporated into a sensor package useful as a liquid level monitoring device. In one embodiment, a plurality of sensor modules may be embodied to determine the level of a particular fluid such as the level of water in a storage tank, the level of fuel in a fluid tank, or the level of a liquid such as water or oil in a well site. An example of such a sensor package is illustrated in FIG. 7B. Referring to FIG. 7B, sensor modules 30 are adjacently positioned in liquid level monitoring device 80 such that when the liquid level is sufficient to immerse a portion of the device, one or more of sensing lengths 26 and/or sensing surfaces 28, corresponding to the portion of the device immersed in the liquid, contacts the liquid medium and generates a signal which is sent to signal processor 18. Monitoring device 80 may optionally include shutters 82 which may be controlled so as to open and allow for the sampling of an environment once the monitoring device has been positioned in the particular environment.

In another embodiment, the optical sensor further includes an analyte-specific coating. This embodiment renders the sensor useful in measuring specific analytes (e.g., chemicals and biochemicals) that may be present in a medium, as well as medium parameters including pH and ionic strength. As used herein, the term "analyte-specific coating" refers to a deposit or coating of a material onto either the optical fiber's sensing length or the fiber's sensing surface. The deposited or coated material interacts with a specific analyte present in a medium and the interaction is measurable by the sensor of the present invention. Basically, the interaction between the analyte-specific coating of the sensor and the specific analyte present in the solution results in some change that is measurable by the evanescent wave produced by the sensor of the present invention. Operationally, on contacting the analyte-specific coating with a medium containing an analyte that specifically interacts with the coating, light loss from the fiber occurs in an amount directly proportional to the amount of specific analyte interacting with the analyte-specific coating. Thus, the presence and, if calibrated, the quantity of a specific analyte present in a medium may be determined.

Figure 8A:
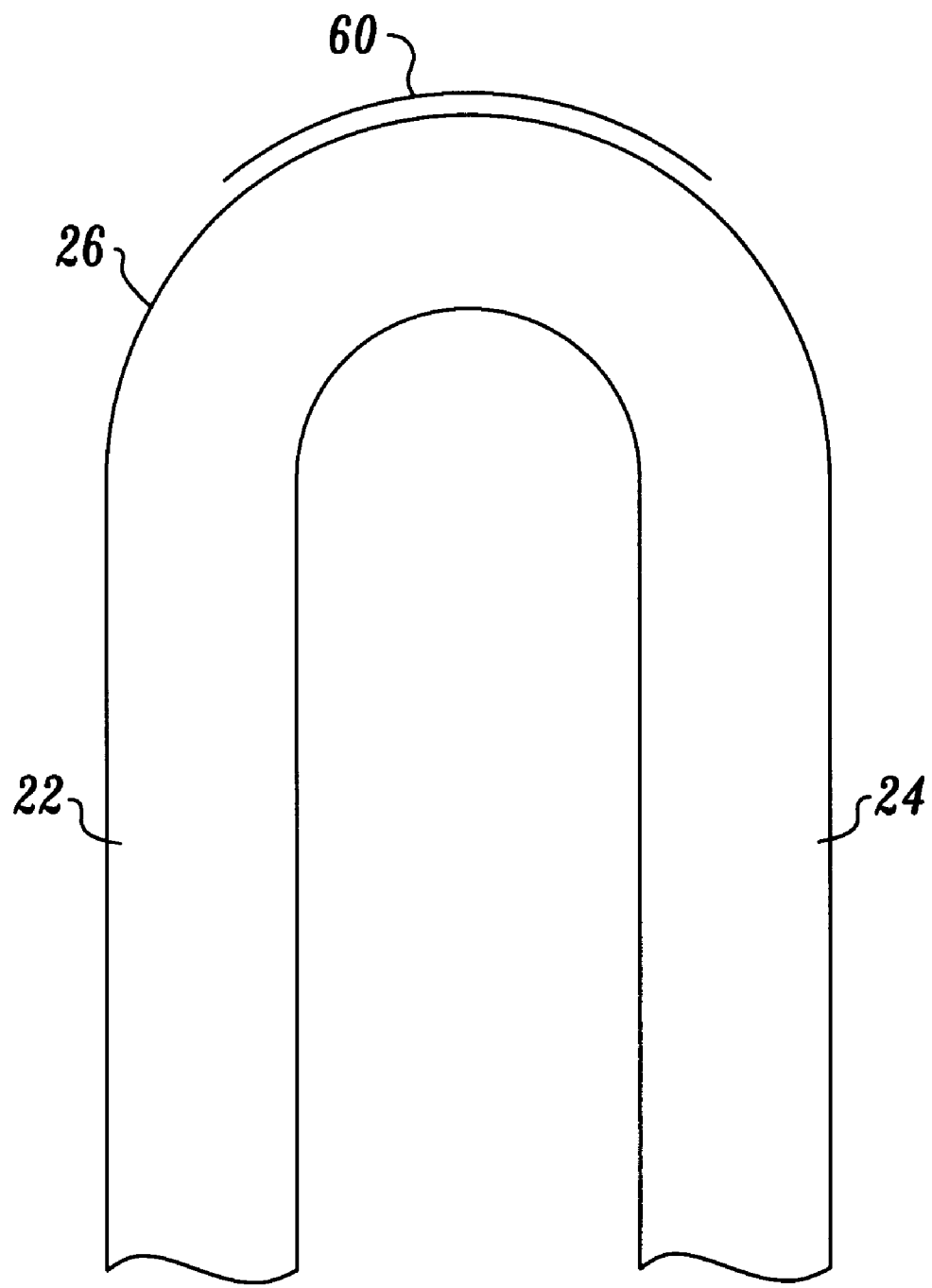
FIGS. 8A and 8B are schematic representations of portions of the optical sensors of the present invention that include an analyte-specific coating.
Figure 8B:
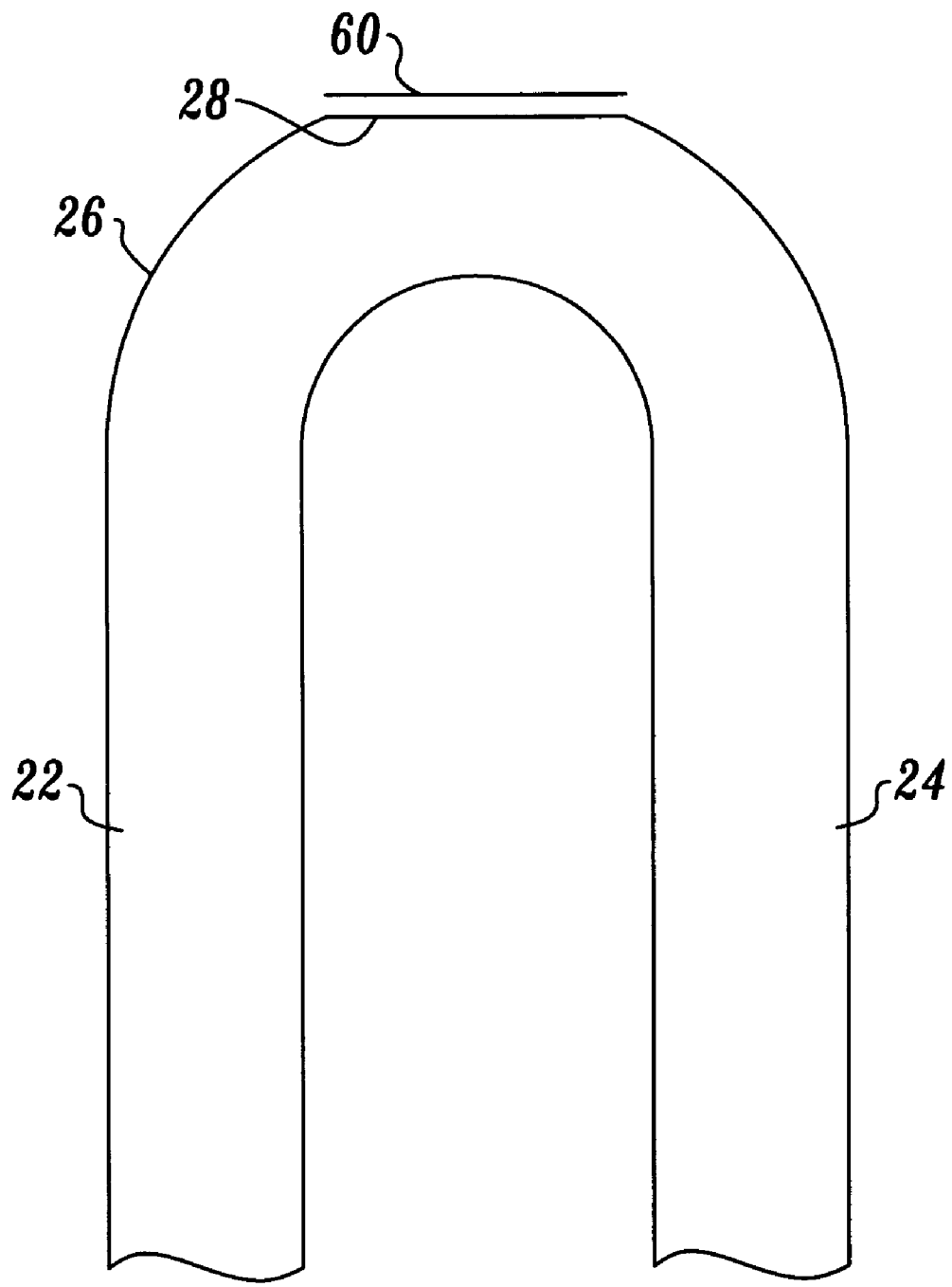

Referring to FIGS. 8A and 8B, analyte-specific coating 60 is applied to and located on the optical sensor's sensing length 26 and sensing surface 28, respectively.

As noted above, the interaction between any two materials that results in a change in the amount light lost from the optical fiber may be suitably measured by the sensor of the present invention. The analyte-specific coating may be a chemical such as an indicator compound; a biochemical or biological molecule such as an enzyme, antibody, or nucleic acid; or a membrane that selectively binds a particular chemical or biochemical. Suitable chemical coatings include, for example, organic and inorganic compounds that, on exposure to a medium containing certain other chemicals, biochemicals, or metal ions, undergo a change in their absorbance properties. The use of specific biochemical binding partners or specific binding pairs, including receptor molecules and their ligands, antibodies and their ligands, and complementary nucleic acid sequences, are also within the scope of this embodiment of the present invention. In such embodiments, one member of the specific binding pair (e.g., a receptor) may serve as analyte-specific coating to detect as the analyte, the other member of the pair (e.g., its ligand). Synthetic membranes that undergo changes in their absorbance properties in response to parameters of a medium, such as pH, ionic strength, or the presence of certain chemicals including metal ions and dissolved gases such as oxygen and carbon dioxide, and biochemicals including biological species, may also be useful as analyte-specific coatings in the sensor of this invention.

In another aspect of the present invention, a method of detecting a medium in an environment is provided. In the method, a medium is detected by contacting the sensing length and/or sensing surface of the optical sensor described above with the medium. When the medium in contact with the sensing length and/or sensing surface absorbs light at the wavelength(s) emitted by the light source, light transmission through the optical fiber is attenuated and the amount of light received at the detector is decreased in an amount proportional to the nature and amount of the medium sensed relative to the light received in the absence of the absorbing medium.

Optical sensors of the present invention that employ broadband light sources and a multimode waveguides are useful in detecting any fluid that has an absorbance band within the bandwidth of the sensor defined by the emission bandwidth of the sensor's light source. The term "broadband light source" refers; to the band of wavelengths emitted by the sensor's light source. The term "multimode waveguide" refers to the capacity of the light conducting material of the input arm, sensing length, and output arm of the sensor to transmit light of all phases.

Figure 9:
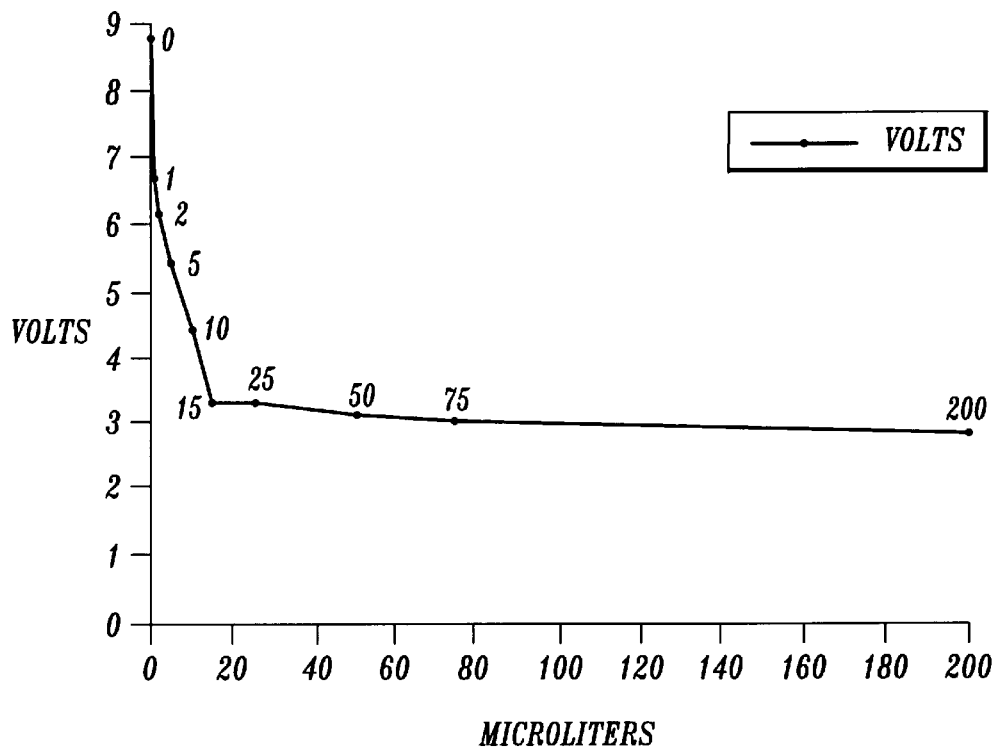
FIG. 9 is a graph that illustrates the sensitivity of a representative optical sensor of this invention in the detection of water.

The characteristics of the optical sensor of the present invention render methods for detecting substances that absorb in the red and/or near-infrared region of the spectrum particularly effective. For example, when the medium sought to be detected is water (or a primarily aqueous medium), the use of a light source emitting at about 850 nm is effective in detecting as little as 0.1 $\mu$L of water present on the sensor's sensing surface. FIG. 9 graphically illustrates the decrease in output signal of a representative optical sensor of this invention as a function of the volume of water in contact with the sensor's planar sensing surface. The sensitivity of representative optical sensors of this invention in the detection of water is presented in Example 2.

The high sensitivity of the method is due to the unique configuration of the sensor of this invention, and also due to the broadband absorbance of water in the near-infrared region of the spectrum. The method takes advantage of the broad near-infrared absorbance of water with the wavelength(s) of light generated by sensor source. The absorbance of water increases greatly from about 400 nm and continues to increase into the far infrared beyond 4000 nm. Thus, the most sensitive methods for detecting water utilizing the sensor of this invention employ wavelengths of light in water's broad absorbance band (i.e., the wavelength (s) at which the greatest amount of the evanescent wave produced by the sensor is absorbed by water in contact with the sensing surface).

As shown in Table 1 of Example 2, the effective detection of water is achieved by the optical sensors of this invention having return bends with R/r about 2.0. For the sensor having a smooth return bend (see Table 1, entry 8), a 58% decrease in output signal was observed when the sensing length was contacted with water. The result demonstrates that the return bend with R/r about 2 is responsible for the high sensitivity achieved by the sensors of the present invention. As indicated in Table 2 of Example 2, the onset of the sensor's high sensitivity occurs when R/r is decreased to less than about 2.5. A dramatic decrease in output signal (87%) was observed for the sensor having a planar sensing surface (see Table 1, entry 9). The result demonstrates that the high sensitivity achieved by the sensors of this invention having a return bend with R/r<2.5 is further enhanced by the presence of the sensing surface located on the apex of the return bend.

Sensitive methods for detecting hydrocarbons, such as those contained in fuels, also exploit the strong absorbances of these substances in the near-infrared region of the spectrum. The near-infrared absorbances are due to C—H bonds present in all hydrocarbons. Typical near-infrared absorbance bands for these substances occur at about 1200 nm (1.2 $\mu$m) and 1400 nm (1.4 $\mu$m) and have bandwidths of about 50 nm. Accordingly, the most sensitive methods for detecting hydrocarbons utilizing the sensor of this invention employ sources emitting light at or near these wavelengths.

Where it is desirable to detect the presence of a substance in an environment, the most sensitive method employs a wavelength of light unique to that substance, i.e., a selective sensor. However, if the detection of a particular class of substances is desired, the method should employ a wavelength band common to all substances in the class. If the detection of one substance in the presence of another is desired, and each has a unique wavelength of absorbance, then either may be detected in the presence of the other by appropriate wavelength selection. The use of a common absorbance wavelength may be successful when one substance absorbs more strongly at the wavelength than the other. In such an instance, the method may utilize a wavelength where the substance present in the lowest amount has the greatest absorbance relative to the absorbance for the predominant substance.

In addition to detecting a substance such as water or a hydrocarbon, the method of the present invention may also be useful in detecting one substance in the presence of another, for example, detecting a substance present in a medium, such as a hydrocarbon in water. The method utilizes the sensor of this invention employing a light source emitting at a wavelength of light commonly absorbed by both substances, but more strongly absorbed by the hydrocarbon. In a preferred embodiment, the method utilizes the sensor of this invention employing a light source emitting at about 950 nm.

The effective and sensitive detection of oil in water by the sensor of this invention is shown in Table 3 of Example 3. In these experiments, the sensors were contacted with the surface of water upon which was dispersed $6 \times 10^{-4}$ $\mu$L oil per square millimeter. As observed in the water sensitivity experiments, no significant output signal decrease was observed for sensors having optical fibers with return bends where R/r>2. However, a significant decrease in signal was observed for the sensors of the present invention having R/r=2.0. For the representative sensor having a smooth return bend, a signal decrease of about 85% was observed (see Table 3, entry 8). A 10-fold greater decrease in signal, a decrease of about 98%, was found for the representative sensor having a sensing surface at the apex of the return bend (see Table 3, entry 9).

These results indicate that the sensors of the present invention are useful in detecting the presence of one fluid, an oil or fuel, in the presence of another, water. Such usefulness is unique to the optical sensors of the present invention and is a distinguishing characteristic over the known optical sensors noted above.

The following examples are offered by way of illustration, not limitation.

EXAMPLES

Example 1

The Manufacture of a Representative Optical Sensor

In this Example, the manufacture of a representative optical sensor of the present invention is described. As noted above, the optical sensor includes a light source, a light detector and signal generator, an optical fiber, and a signal processor. The signal processor is an electronic circuit having the components arranged on a circuitboard in a configuration as described above and as shown in the circuit diagram in FIGS. 3A and 3B. The sensor is assembled by preparing the optical fiber, mounting one end of the fiber into the light source (i.e., the photocell or light-emitting diode), mounting the other end of the fiber into the light detector, securing the fiber to the source and detector through the use of either black adhesive tape or heatshrink tubing, and soldering the light source and light detector on the circuitboard as indicated in the circuit diagram. Depending upon the particular application, the assembly including optical fiber, light source and detector, and circuitboard may be installed in a suitable housing.

The optical fiber is prepared by cutting a piece of fiber to the desired length and polishing its ends. The cladding is then removed from the fiber over the sensing length portion of the optical fiber. The fiber is then bent into the desired return bend configuration by warming and bending around a cylinder having the desired bend radius. If the optical sensor is to include a sensing surface, the sensing surface is prepared by machining the optical fiber such that a planar surface is formed at the apex of the return bend of the optical fiber.

To evaluate the performance characteristics of the sensors of this invention, representative optical sensors were assembled as described above. The sensors included a 1000 $\mu$m (0.04 inch, r=0.02 inch) diameter polymethylmethacrylate optical fiber (AMP Optimate), a light-emitting diode having a peak emission at 950 nm (SFH450, Siemens Optoelectronics, Inc.), and a phototransistor (SFH350, Siemens Optoelectronics, Inc.), and accompanying electronic circuitry as shown in FIGS. 3A and 3B. For the optical sensor having a sensing surface, a planar surface having a length of 0.040 inch was prepared by machining the apex of the return bend of the fiber. The performance characteristics of the representative optical sensors assembled from the components noted above are presented in Examples 2 and 3.

Example 2

Performance Characteristics of Representative Optical Sensors: Water Sensitivity In this Example, the performance characteristics of representative optical sensors prepared as described above in Example 1 are summarized. The sensitivity of the optical sensors in detecting water was compared to other optical fiber-based sensing devices having identical light source, detector, and signal processor, and differing only in the configuration of the optical fiber (i.e., bend radius and sensing surface). The water sensitivity of each of the sensors was determined by immersing the sensing length of each in water. The sensing length for each was prepared by removing the cladding on a 0.7 inch portion of the fiber. The signal-processing circuit was set for a regulated 6.5 volts DC supply with a 5.0 volt output of the sensor. For each sensor output signal measurements were made in air, water, and again in air after drying subsequent to water immersion. The results are summarized in Table 1.

TABLE 1

Sensitivity of sensor output signal as a function of optical fiber configuration: water detection

| Configuration | Bend Radius R (inches) | R/r | Output Signal (volts) | | | Signal Decrease (%) |
|---|---|---|---|---|---|---|
| | | | Air | Water | Dry | |
| 1 no bend | — | — | 5.00 | 5.00 | 5.00 | — |
| 2 | 1.33 | 66.5 | 5.00 | 5.00 | 5.00 | — |
| 3 | 0.41 | 20.5 | 4.98 | 4.98 | 4.98 | — |
| 4 | 0.28 | 14.0 | 4.97 | 4.96 | 4.97 | <1 |
| 5 | 0.25 | 13.0 | 4.97 | 4.96 | 4.97 | <1 |
| 6 | 0.15 | 7.5 | 4.95 | 4.92 | 4.95 | <1 |
| 7 | 0.10 | 5.0 | 4.93 | 4.87 | 4.92 | 1.2 |
| 8 smooth bend | 0.04 | 2.0 | 4.91 | 2.08 | 4.91 | 58 |
| 9 sensing surface | 0.04 | 2.0 | 4.80 | 0.63 | 4.80 | 87 |

The results in Table 1 show that the representative optical sensors of the present invention having R/r=2.0 were the most sensitive sensors. The results demonstrate that the sharp return bend of the optical fiber of the sensors of the present invention are critical in providing a highly sensitive sensor for detecting water.

Referring to Table 1 above, less than a 1% decrease in output signal was observed until the optical fiber bend radius was decreased to a value of R/r of about 7.5. A decrease in R/r to 5.0 provided only a 1.2% decrease in output signal. A dramatic decrease in output signal of about 58% was observed for a representative sensor of the present invention with R/r=2.0 (see Table 1, entry 8). Furthermore, the representative optical sensor having a planar sensing surface provided enhanced sensitivity compared to the sensor having a smooth return bend. On contact with water, the decrease in output signal for the sensor having a planar sensing surface was observed to be about 87% (see Table 1, entry 9).

The stability of the sensor of this invention is demonstrated by the output signal observed after blow drying the fiber. In each case, the output signal returned to its original value in air indicating that the sensor may be reliably used to continuously monitor changes in its environment.

To more closely examine the effect of sensor configuration, particularly the sensitivity of bend radius (i.e., R/r) on the sensors' detection of water, the output signal for several optical fiber configurations, each having a smooth bend, was measured as described above. The results are summarized in Table 2.

TABLE 2

Sensitivity of sensor output signal as a function of optical fiber configuration: water detection

| Configuration | R/r | Air | Water | Signal Decrease (%) |
|---|---|---|---|---|
| 1 | 3.25 | 4.86 | 4.77 | 1.9 |
| 2 | 3.05 | 4.83 | 4.70 | 2.7 |
| 3 | 2.75 | 4.82 | 4.66 | 3.3 |
| 4 | 2.50 | 4.73 | 3.68 | 22 |

The results of Table 2 demonstrate that the sensor output signal decreases dramatically with R/r and that high sensor sensitivity onset occurs at about R/r=2.50. Accordingly, the optical sensors of the present invention have R/r≦2.50, and preferably R/r about 2.0.

Example 3

Performance Characteristics of a Representative Optical Sensor: Oil in Water Sensitivity In this Example, the performance characteristics of representative optical sensor of the present invention in detecting the presence of oil in water are described. The optical sensors used in this Example were prepared as described in Examples 1 and 2 above. An oil-in-water mixture was prepared by dropping 20 μL of oil (SAE 30 motor oil) into a container filled with water and having a surface area of about 33,000 mm$^2$ and allowing the oil to spread over the surface of the water overnight. The sensing length for each optical fiber for each sensor was contacted with the water's surface and the signal output recorded. The results are presented in Table 3.

TABLE 3

Sensitivity of sensor output signal as a function of optical fiber configuration: oil in water detection

| Configuration | Bend Radius R (inches) | R/r | Output Signal (volts) | | Signal Decrease (%) |
|---|---|---|---|---|---|
| | | | Air | Oil/Water | |
| 1 no bend | — | — | 5.01 | 5.01 | — |
| 2 | 1.33 | 66.5 | 5.01 | 5.01 | — |
| 3 | 0.41 | 20.5 | 4.99 | 4.99 | — |
| 4 | 0.28 | 14.0 | 4.99 | 4.99 | — |
| 5 | 0.25 | 13.0 | 4.99 | 4.99 | — |
| 6 | 0.15 | 7.5 | 4.97 | 4.98 | — |
| 7 | 0.10 | 5.0 | 4.97 | 4.88 | 1.8 |
| 8 smooth bend | 0.04 | 2.0 | 4.87 | 0.51–0.90 | 86 |
| 9 sensing surface | 0.04 | 2.0 | 4.80 | 0.013–0.065 | 99 |

The results in Table 3 show that the most sensitive detection of oil in water is achieved using the representative optical sensors of the present invention having R/r=2.0. A dramatic decrease in the signal output (on average about an 86% decrease) is observed for the optical sensor of the present invention having a smooth return bend (see Table 3, entry 8) compared to the other sensors having greater bend radii. The observed decrease is also significantly greater than that observed when the sensor was contacted with water alone as shown in Example 2, Table 1, entry 8. The optical sensor having a planar sensing surface (see Table 3, entry 9) shows about a tenfold greater change in signal output (on average about a 99% decrease) upon contact with the oil-in-water surface as compared to water alone. The large decreases in output signal noted above were observed by contacting the sensor's sensing length with the water's surface upon which was dispersed about $6 \times 10^{-4}$ µL oil per square millimeter. These results illustrate that the sensitivity of the optical sensors in detecting oil in water is significantly greater than their sensitivity to water alone, and thus the sensors are ideal for monitoring the presence of oils in water and useful in continuous monitoring of ground water or water supplies for contamination by hydrocarbons such as fuels and oils.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A sensor system comprising:
    an enclosure for a fluid-sensitive cable connection, the enclosure having input and output ports for receiving input and output cables extending from the fluid-sensitive connection within the enclosure, through the ports to the outside of the enclosure; and
    a fluid sensor positioned in the enclosure for detecting and signaling the presence of a fluid within the enclosure,
    wherein the fluid-sensitive connection is selected from the group consisting of electronic and communication connections.

2. A sensor system comprising:
    an enclosure for a fluid-sensitive component; and
    a fluid sensor positioned in the enclosure for detecting and signaling the presence of a fluid within the enclosure,
    wherein the fluid-sensitive component is selected from the group consisting of electronic and communication connections; and
    wherein the enclosure comprises a means for conducting fluid to the sensor.

3. The sensor system of claim 2 wherein the means for conducting fluid to the sensor is a groove.

4. The sensor system of claim 2 further comprising an absorbent material in the enclosure and positioned to absorb fluid to protect a fluid-sensitive component in the enclosure.

5. The sensor system of claim 4 wherein the absorbent material comprises a superabsorbent polymeric material.

6. The sensor system of claim 2 wherein the sensor is an optical sensor, comprising:
    (a) a light source for generating light;
    (b) a light detector and signal generator for receiving light from the light source and for generating variable signals dependent on the amount of light received; and
    (c) an optical fiber made of a light conducting material extending between the light source and the light detector and having a sensing length comprising a return bend in the optical fiber forming an apex, wherein the return bend has a bend radius less than or equal to about 2.5 times the radius of the optical fiber.

7. The sensor system of claim 2 wherein the sensor is an optical sensor, comprising:
    (a) a light source for generating light;
    (b) a light detector and signal generator for receiving light from the light source and for generating variable signals dependent on the amount of light received; and
    (c) an optical fiber made of a light conducting material extending between the light source and the light detector and having a sensing length comprising a return bend in the optical fiber forming an apex, wherein the return bend has a bend radius less than or equal to about 2.5 times the radius of the optical fiber, wherein the sensing length further comprises a planar sensing surface at the apex of the return bend, and wherein the planar sensing surface has a maximum length of about twice the radius of the return bend.

8. A sensor system comprising:
    an enclosure;
    a fluid-sensitive component mounted in the enclosure; and
    a fluid sensor positioned in the enclosure for detecting and signaling the presence of a fluid within the enclosure,
    wherein the fluid-sensitive component is selected from the group consisting of electronic and communication connections; and
    wherein the enclosure comprises a means for conducting fluid to the sensor.

9. The sensor system of claim 8 wherein the enclosure is normally fluid-tight, the fluid-sensitive component being a cable splice, the enclosure being adapted for mounting the cable splice therein.

10. The sensor system of claim 9 further comprising an absorbent material mounted in the enclosure and positioned to absorb the fluid to protect the cable splice.

11. The sensor system of claim 10 wherein the absorbent material comprises a superabsorbent polymeric material.

12. The sensor system of claim 10 wherein the fluid is water.

13. The sensor system of claim 9 wherein the sensor is an optical sensor, comprising:
    (a) a light source for generating light;
    (b) a light detector and signal generator for receiving light from the light source and for generating variable signals dependent on the amount of light received; and
    (c) an optical fiber made of a light conducting material extending between the light source and the light detector and having a sensing length comprising a return bend in the optical fiber forming an apex, wherein the return bend has a bend radius less than or equal to about 2.5 times the radius of the optical fiber.

14. The sensor system of claim 9 wherein the sensor is an optical sensor, comprising:
    (a) a light source for generating light;
    (b) a light detector and signal generator for receiving light from the light source and for generating variable signals dependent on the amount of light received; and
    (c) an optical fiber made of a light conducting material extending between the light source and the light detector and having a sensing length comprising a return bend in the optical fiber forming an apex, wherein the return bend has a bend radius less than or equal to about 2.5 times the radius of the optical fiber, wherein the sensing length further comprises a planar sensing surface at the apex of the return bend, and wherein the planar sensing surface has a maximum length of about twice the radius of the return bend.

15. The sensor system of claim 9 wherein the enclosure comprises a closure base, a closure dome having cable ports, a splice tray attached to the closure dome, a means for sealing the dome to the base, and a means for securing the dome to the base; and wherein the sensor system comprises the sensor, a means for conducting fluid to the sensor, and an absorbent material mounted in the enclosure and positioned to absorb the fluid to protect the cable splice.

16. The sensor system of claim 15 wherein the means for conducting fluid to the sensor is an internal groove in the closure base.

17. The sensor system of claim 15 wherein the absorbent material is a continuous ring mounted in the closure base between the sensor and the fluid-sensitive component.

18. The sensor system of claim 15 wherein the sensor is an optical sensor, comprising:
(a) a light source for generating light;
(b) a light detector and signal generator for receiving light from the light source and for generating variable signals dependent on the amount of light received; and
(c) an optical fiber made of a light conducting material extending between the light source and the light detector and having a sensing length comprising a return bend in the optical fiber forming an apex, wherein the return bend has a bend radius less than or equal to about 2.5 times the radius of the optical fiber.

19. The system of claim 15 wherein the sensor is an optical sensor, comprising:
(a) a light source for generating light;
(b) a light detector and signal generator for receiving light from the light source and for generating variable signals dependent on the amount of light received; and
(c) an optical fiber made of a light conducting material extending between the light source and the light detector and having a sensing length comprising a return bend in the optical fiber forming an apex, wherein the return bend has a bend radius less than or equal to about 2.5 times the radius of the optical fiber, wherein the sensing length further comprises a planar sensing surface at the apex of the return bend, and wherein the planar sensing surface has a maximum length of about twice the radius of the return bend.

20. The sensor system of claim 8 wherein the fluid-sensitive component is an electrical component.

21. The sensor system of claim 8 wherein the fluid-sensitive component is an optical fiber component.

22. The sensor system of claim 8 wherein the fluid is water.

23. The sensor system of claim 8 wherein the sensor is an optical sensor, comprising:
(a) a light source for generating light;
(b) a light detector and signal generator for receiving light from the light source and for generating variable signals dependent on the amount of light received; and
(c) an optical fiber made of a light conducting material extending between the light source and the light detector and having a sensing length comprising a return bend in the optical fiber forming an apex, wherein the return bend has a bend radius less than or equal to about 2.5 times the radius of the optical fiber.

24. The sensor system of claim 8 wherein the sensor is an optical sensor, comprising:
(a) a light source for generating light;
(b) a light detector and signal generator for receiving light from the light source and for generating variable signals dependent on the amount of light received; and
(c) an optical fiber made of a light conducting material extending between the light source and the light detector and having a sensing length comprising a return bend in the optical fiber forming an apex, wherein the return bend has a bend radius less than or equal to about 2.5 times the radius of the optical fiber, wherein the sensing length further comprises a planar sensing surface at the apex of the return bend, and wherein the planar sensing surface has a maximum length of about twice the radius of the return bend.

25. A sensor system comprising:
an enclosure for a fluid-sensitive component; and
a fluid sensor positioned in the enclosure for detecting and signaling the presence of a fluid within the enclosure, wherein the sensor is an optical sensor comprising:
(a) a light source for generating light;
(b) a light detector and signal generator for receiving light from the light source and for generating variable signals dependent on the amount of light received; and
(c) an optical fiber made of a light conducting material extending between the light source and the light detector and having a sensing length comprising a return bend in the optical fiber forming an apex, wherein the return bend has a bend radius less than or equal to about 2.5 times the radius of the optical fiber.

26. A sensor system comprising:
an enclosure for a fluid-sensitive component; and
a fluid sensor positioned in the enclosure for detecting and signaling the presence of a fluid within the enclosure, wherein the sensor is an optical sensor comprising:
(a) a light source for generating light;
(b) a light detector and signal generator for receiving light from the light source and for generating variable signals dependent on the amount of light received; and
(c) an optical fiber made of a light conducting material extending between the light source and the light detector and having a sensing length comprising a return bend in the optical fiber forming an apex, wherein the return bend has a bend radius less than or equal to about 2.5 times the radius of the optical fiber, wherein the sensing length further comprises a planar sensing surface at the apex of the return bend, and wherein the planar sensing surface has a maximum length of about twice the radius of the return bend.

27. A sensor system comprising:
an enclosure;
a fluid-sensitive component mounted in the enclosure; and
a fluid sensor positioned in the enclosure for detecting and signaling the presence of a fluid within the enclosure, wherein the sensor is an optical sensor comprising:
(a) a light source for generating light;
(b) a light detector and signal generator for receiving light from the light source and for generating variable signals dependent on the amount of light received; and
(c) an optical fiber made of a light conducting material extending between the light source and the light detector and having a sensing length comprising a return bend in the optical fiber forming an apex, wherein the return bend has a bend radius less than or equal to about 2.5 times the radius of the optical fiber.

28. A sensor system comprising:
an enclosure;
a fluid-sensitive component mounted in the enclosure; and
a fluid sensor positioned in the enclosure for detecting and signaling the presence of a fluid within the enclosure, wherein the sensor is an optical sensor comprising:
(a) a light source for generating light;
(b) a light detector and signal generator for receiving light from the light source and for generating variable signals dependent on the amount of light received; and
(c) an optical fiber made of a light conducting material extending between the light source and the light detector and having a sensing length comprising a return bend in the optical fiber forming an apex, wherein the return bend has a bend radius less than or equal to about 2.5 times the radius of the optical fiber, wherein the sensing length further comprises a planar sensing surface at the apex of the return bend, and wherein the planar sensing surface has a maximum length of about twice the radius of the return bend.

29. A sensor system comprising:

an enclosure;

a fluid-sensitive component mounted in the enclosure; and a fluid sensor positioned in the enclosure for detecting and signaling the presence of a fluid within the enclosure, wherein the enclosure is normally fluidtight, the fluid-sensitive component being a cable splice, the enclosure being adapted for mounting the cable splice therein, and wherein the sensor is an optical sensor comprising:
(a) a light source for generating light;
(b) a light detector and signal generator for receiving light from the light source and for generating variable signals dependent on the amount of light received; and
(c) an optical fiber made of a light conducting material extending between the light source and the light detector and having a sensing length comprising a return bend in the optical fiber forming an apex, wherein the return bend has a bend radius less than or equal to about 2.5 times the radius of the optical fiber.

30. A sensor system comprising:

an enclosure;

a fluid-sensitive component mounted in the enclosure; and a fluid sensor positioned in the enclosure for detecting and signaling the presence of a fluid within the enclosure, wherein the enclosure is normally fluidtight, the fluid-sensitive component being a cable splice, the enclosure being adapted for mounting the cable splice therein, and wherein the sensor is an optical sensor comprising:
(a) a light source for generating light;
(b) a light detector and signal generator for receiving light from the light source and for generating variable signals dependent on the amount of light received; and
(c) an optical fiber made of a light conducting material extending between the light source and the light detector and having a sensing length comprising a return bend in the optical fiber forming an apex, wherein the return bend has a bend radius less than or equal to about 2.5 times the radius of the optical fiber, wherein the sensing length further comprises a planar sensing surface at the apex of the return bend, and wherein the planar sensing surface has a maximum length of about twice the radius of the return bend.

31. A sensor system comprising:

an enclosure;

a fluid-sensitive component mounted in the enclosure; and a fluid sensor positioned in the enclosure for detecting and signaling the presence of a fluid within the enclosure, wherein the enclosure is normally fluidtight, the fluid-sensitive component being a cable splice, the enclosure being adapted for mounting the cable splice therein, and wherein the enclosure comprises a closure base, a closure dome having cable ports, a splice tray attached to the closure dome, a means for sealing the dome to the base, and a means for securing the dome to the base; and wherein the sensor system comprises the sensor, a means for conducting fluid to the sensor, and an absorbent material mounted in the enclosure and positioned to absorb the fluid to protect the cable splice.

32. The sensor system of claim 31 wherein the means for conducting fluid to the sensor is an internal groove in the closure base.

33. The sensor system of claim 31 wherein the absorbent material is a continuous ring mounted in the closure base between the sensor and the fluid-sensitive component.

34. The sensor system of claim 31 wherein the sensor is an optical sensor comprising:
(a) a light source for generating light;
(b) a light detector and signal generator for receiving light from the light source and for generating variable signals dependent on the amount of light received; and
(c) an optical fiber made of a light conducting material extending between the light source and the light detector and having a sensing length comprising a return bend in the optical fiber forming an apex, wherein the return bend has a bend radius less than or equal to about 2.5 times the radius of the optical fiber.

35. The system of claim 31 wherein the sensor is an optical sensor comprising:
(a) a light source for generating light;
(b) a light detector and signal generator for receiving light from the light source and for generating variable signals dependent on the amount of light received; and
(c) an optical fiber made of a light conducting material extending between the light source and the light detector and having a sensing length comprising a return bend in the optical fiber forming an apex, wherein the return bend has a bend radius less than or equal to about 2.5 times the radius of the optical fiber, wherein the sensing length further comprises a planar sensing surface at the apex of the return bend, and wherein the planar sensing surface has a maximum length of about twice the radius of the return bend.

* * * * *